United States Patent
De Lemos et al.

(10) Patent No.: US 9,295,806 B2
(45) Date of Patent: Mar. 29, 2016

(54) SYSTEM AND METHOD FOR DETERMINING EMOTIONAL RESPONSE TO OLFACTORY STIMULI

(75) Inventors: Jakob De Lemos, Copenhagen (DK); Ole Baunbaek Jensen, Copenhagen (DK); Golam Reza Sadeghnia, Copenhagen (DK)

(73) Assignee: iMotions A/S, Copenhagen (DK)

( * ) Notice: Subject to any disclaimer, the term of this patent is extended or adjusted under 35 U.S.C. 154(b) by 1240 days.

(21) Appl. No.: 13/255,010

(22) PCT Filed: Mar. 5, 2010

(86) PCT No.: PCT/IB2010/000821
§ 371 (c)(1),
(2), (4) Date: Dec. 12, 2011

(87) PCT Pub. No.: WO2010/100567
PCT Pub. Date: Sep. 10, 2010

(65) Prior Publication Data
US 2012/0078065 A1    Mar. 29, 2012

Related U.S. Application Data

(60) Provisional application No. 61/158,197, filed on Mar. 6, 2009.

(51) Int. Cl.
*A61B 5/00*      (2006.01)
*A61M 21/00*      (2006.01)
(Continued)

(52) U.S. Cl.
CPC ............... *A61M 21/00* (2013.01); *A61B 3/113* (2013.01); *A61B 5/16* (2013.01); *A61B 5/165* (2013.01);
(Continued)

(58) Field of Classification Search
None
See application file for complete search history.

(56) References Cited

U.S. PATENT DOCUMENTS

| 3,507,988 A | 4/1970 | Holmes |
| 3,712,716 A | 1/1973 | Cornsweet et al. ............... 351/7 |

(Continued)

FOREIGN PATENT DOCUMENTS

| EP | 0 883 049 A1 | 12/1998 |
| JP | H07-313494 | 12/1995 |

(Continued)

OTHER PUBLICATIONS

Anderson, Keith, "Real-Time Emotion Recognition Using Biologically Inspired Models", Department of Computer Science, Queen Mary College, University of London, [no date], 8 pages.

(Continued)

*Primary Examiner* — Brian T Gedeon
*Assistant Examiner* — Ankit Tejani
(74) *Attorney, Agent, or Firm* — Sheppard Mullin Richter & Hampton LLP

(57) ABSTRACT

Systems and methods are provided for determining pre-cognitive and/or cognitive emotional response to predetermined olfactory stimuli. Among other things, the invention may include exposing a test subject to a controlled flow of a predetermined olfactory stimulus, measuring eye data (e.g., using an eye tracking device) corresponding to when the olfactory stimulus reached the subject's nose, and analyzing and processing the eye data for determining the subject's emotional response to the olfactory stimulus. In some implementations, the invention may include measuring the test subject's respiratory parameters so as to deliver the predetermined olfactory stimulus at a certain point in the test subjects respiratory cycle.

8 Claims, 6 Drawing Sheets

(51) Int. Cl.
  *A61B 3/113* (2006.01)
  *A61B 5/16* (2006.01)
  *A61M 16/16* (2006.01)
  *A61M 16/00* (2006.01)

(52) U.S. Cl.
  CPC ............ *A61B 5/4011* (2013.01); *A61M 16/161* (2014.02); *A61M 2016/0021* (2013.01); *A61M 2016/0033* (2013.01); *A61M 2021/0016* (2013.01); *A61M 2205/3368* (2013.01); *A61M 2205/3375* (2013.01); *A61M 2205/80* (2013.01); *A61M 2230/18* (2013.01); *A61M 2230/432* (2013.01); *A61M 2230/63* (2013.01)

(56) References Cited

U.S. PATENT DOCUMENTS

| | | | |
|---|---|---|---|
| 3,827,789 A | 8/1974 | Molner et al. | 351/23 |
| 3,986,030 A | 10/1976 | Teltscher | 250/349 |
| 4,034,401 A | 7/1977 | Mann | 358/93 |
| 4,075,657 A | 2/1978 | Weinblatt | 358/93 |
| 4,146,311 A | 3/1979 | Murr | 351/24 |
| 4,483,681 A | 11/1984 | Weinblatt | 434/236 |
| 4,528,989 A | 7/1985 | Weinblatt | 128/745 |
| 4,574,314 A | 3/1986 | Weinblatt | 358/227 |
| 4,582,403 A | 4/1986 | Weinblatt | 351/210 |
| 4,623,230 A | 11/1986 | Weinblatt | 351/210 |
| 4,647,964 A | 3/1987 | Weinblatt | 358/84 |
| 4,649,434 A | 3/1987 | Weinblatt | 358/250 |
| 4,659,197 A | 4/1987 | Weinblatt | 351/210 |
| 4,661,847 A | 4/1987 | Weinblatt | 358/108 |
| 4,670,264 A | 6/1987 | Warren et al. | 424/195.1 |
| 4,670,463 A | 6/1987 | Warren et al. | 514/464 |
| 4,695,879 A | 9/1987 | Weinblatt | 358/84 |
| 4,718,106 A | 1/1988 | Weinblatt | 455/2 |
| 4,837,851 A | 6/1989 | Weinblatt | 455/67 |
| 4,931,865 A | 6/1990 | Scarampi | 358/84 |
| 4,974,010 A | 11/1990 | Cleveland et al. | 354/403 |
| 4,992,867 A | 2/1991 | Weinblatt | 358/108 |
| 5,090,797 A | 2/1992 | Cleveland et al. | 351/210 |
| 5,202,355 A | 4/1993 | Nakatsu | 514/568 |
| 5,204,703 A | 4/1993 | Hutchinson et al. | 351/210 |
| 5,219,322 A | 6/1993 | Weathers | 600/27 |
| 5,231,674 A | 7/1993 | Cleveland et al. | 382/6 |
| 5,243,517 A | 9/1993 | Schmidt et al. | 364/419.2 |
| 5,318,442 A | 6/1994 | Jeffcoat et al. | 433/72 |
| 5,380,540 A | 1/1995 | Yamanaka et al. | 426/534 |
| 5,406,956 A | 4/1995 | Farwell | 128/731 |
| 5,517,021 A | 5/1996 | Kaufman et al. | 250/221 |
| 5,617,855 A | 4/1997 | Waletzky et al. | 128/653.1 |
| 5,649,061 A | 7/1997 | Smyth | 395/20 |
| 5,676,138 A | 10/1997 | Zawilinski | 128/630 |
| 5,725,472 A | 3/1998 | Weathers | 600/21 |
| 5,884,626 A | 3/1999 | Kuroda et al. | 128/630 |
| 5,912,721 A | 6/1999 | Yamaguchi et al. | 351/210 |
| 6,021,346 A | 2/2000 | Ryu et al. | 600/544 |
| 6,067,842 A | 5/2000 | Gygax et al. | 73/23.34 |
| 6,090,051 A | 7/2000 | Marshall | 600/558 |
| 6,102,870 A | 8/2000 | Edwards | 600/558 |
| 6,120,461 A | 9/2000 | Smyth | 600/558 |
| 6,151,571 A | 11/2000 | Pertrushin | 704/209 |
| 6,163,281 A | 12/2000 | Torch | 341/21 |
| 6,190,314 B1 | 2/2001 | Ark et al. | 600/300 |
| 6,228,038 B1 | 5/2001 | Claessens | 600/558 |
| 6,275,806 B1 | 8/2001 | Pertrushin | 704/272 |
| 6,292,688 B1 | 9/2001 | Patton | 600/544 |
| 6,298,263 B1 | 10/2001 | Sedgwick et al. | 600/544 |
| 6,325,475 B1 * | 12/2001 | Hayes | A61B 5/00 128/203.11 |
| 6,346,887 B1 | 2/2002 | Van Orden et al. | 340/575 |
| 6,353,810 B1 | 3/2002 | Petrushin | 704/236 |
| 6,385,590 B1 | 5/2002 | Levine | 705/10 |
| 6,401,050 B1 | 6/2002 | Cooke et al. | 702/127 |
| 6,422,999 B1 | 7/2002 | Hill | 600/300 |
| 6,427,137 B2 | 7/2002 | Petrushin | 704/273 |
| 6,429,868 B1 | 8/2002 | Dehner, Jr. et al. | 345/440 |
| 6,434,419 B1 | 8/2002 | Gevins et al. | 600/544 |
| 6,453,194 B1 | 9/2002 | Hill | 600/546 |
| 6,463,415 B2 | 10/2002 | St. John | 704/273 |
| 6,463,786 B1 | 10/2002 | Behan et al. | 73/23.34 |
| 6,480,826 B2 | 11/2002 | Pertrushin | 704/270 |
| 6,572,562 B2 | 6/2003 | Marshall | 600/558 |
| 6,585,521 B1 | 7/2003 | Obrador | 434/236 |
| 6,598,971 B2 | 7/2003 | Cleveland | 351/209 |
| 6,638,217 B1 | 10/2003 | Liberman | 600/300 |
| 6,697,457 B2 | 2/2004 | Petrushin | 379/88.08 |
| 6,826,540 B1 | 11/2004 | Plantec et al. | 705/10 |
| 6,862,497 B2 | 3/2005 | Kemp et al. | 700/264 |
| 6,873,314 B1 | 3/2005 | Campbell | 345/156 |
| 6,879,709 B2 | 4/2005 | Tian et al. | 382/118 |
| 6,978,243 B2 | 12/2005 | Godinot et al. | 705/1 |
| 7,027,621 B1 | 4/2006 | Prokoski | 382/118 |
| 7,110,582 B1 | 9/2006 | Hay | 382/128 |
| 7,113,916 B1 | 9/2006 | Hill | 705/10 |
| 7,120,880 B1 | 10/2006 | Dryer et al. | 715/863 |
| 7,155,159 B1 | 12/2006 | Weinblatt et al. | 455/2.01 |
| 7,191,403 B2 | 3/2007 | Crain et al. | 715/760 |
| 7,246,081 B2 | 7/2007 | Hill | 705/10 |
| 7,302,475 B2 | 11/2007 | Gold et al. | 709/217 |
| 7,306,337 B2 | 12/2007 | Ji et al. | 351/209 |
| 7,356,470 B2 | 4/2008 | Roth et al. | 704/270 |
| 7,401,920 B1 | 7/2008 | Kranz et al. | 351/210 |
| 7,593,952 B2 | 9/2009 | Soll et al. | 707/102 |
| 7,657,062 B2 | 2/2010 | Pilu | 382/103 |
| 7,689,499 B1 | 3/2010 | Duquette | 705/37 |
| 7,740,631 B2 | 6/2010 | Bleich et al. | 606/79 |
| 7,747,068 B1 | 6/2010 | Smyth et al. | 382/154 |
| 7,881,493 B1 | 2/2011 | Edwards et al. | 382/103 |
| 8,136,944 B2 | 3/2012 | De Lemos | 351/209 |
| 8,814,357 B2 | 8/2014 | De Lemos | 351/209 |
| 8,986,218 B2 | 3/2015 | De Lemos et al. | 600/558 |
| 2002/0007105 A1 | 1/2002 | Prabhu et al. | 600/26 |
| 2002/0037533 A1 | 3/2002 | Civelli et al. | 435/7.1 |
| 2002/0091654 A1 | 7/2002 | Alroy | 706/21 |
| 2002/0105427 A1 | 8/2002 | Hamamoto et al. | 340/576 |
| 2002/0133347 A1 | 9/2002 | Schoneburg et al. | 704/257 |
| 2002/0135618 A1 | 9/2002 | Maes et al. | 345/767 |
| 2003/0001846 A1 | 1/2003 | Davis et al. | 345/474 |
| 2003/0040921 A1 | 2/2003 | Hughes et al. | 705/1 |
| 2003/0046401 A1 | 3/2003 | Abbott et al. | 709/228 |
| 2003/0078838 A1 | 4/2003 | Szmanda | 705/14 |
| 2003/0123027 A1 | 7/2003 | Amir et al. | 351/209 |
| 2003/0125610 A1 | 7/2003 | Sachs et al. | 600/300 |
| 2004/0009462 A1 | 1/2004 | McElwrath | 434/350 |
| 2004/0044495 A1 | 3/2004 | Lampert et al. | 702/127 |
| 2004/0092809 A1 | 5/2004 | DeCharms | 600/410 |
| 2004/0098298 A1 | 5/2004 | Yin | 705/10 |
| 2004/0193068 A1 | 9/2004 | Burton et al. | 600/544 |
| 2004/0210159 A1 | 10/2004 | Kibar | 600/558 |
| 2004/0249650 A1 | 12/2004 | Freedman et al. | 705/1 |
| 2005/0075532 A1 | 4/2005 | Lee et al. | 600/27 |
| 2005/0132290 A1 | 6/2005 | Buchner et al. | 715/702 |
| 2005/0175218 A1 | 8/2005 | Vertegaal et al. | 382/103 |
| 2005/0221268 A1 | 10/2005 | Chaar et al. | 434/350 |
| 2005/0225723 A1 | 10/2005 | Pilu | 351/209 |
| 2005/0228785 A1 | 10/2005 | Wolcott et al. | 707/3 |
| 2005/0234779 A1 | 10/2005 | Chiu et al. | 705/24 |
| 2005/0289582 A1 | 12/2005 | Tavares et al. | 725/10 |
| 2006/0030907 A1 | 2/2006 | McNew | 607/88 |
| 2006/0049957 A1 | 3/2006 | Surgenor et al. | 340/825.19 |
| 2006/0064037 A1 | 3/2006 | Shalon et al. | 600/586 |
| 2006/0074742 A1 | 4/2006 | Santandrea | 705/10 |
| 2006/0082206 A1 | 4/2006 | Travis | 297/423.1 |
| 2006/0110008 A1 | 5/2006 | Vertegaal et al. | 382/103 |
| 2006/0167371 A1 | 7/2006 | Flaherty et al. | 600/545 |
| 2006/0167530 A1 | 7/2006 | Flaherty et al. | 607/62 |
| 2006/0189900 A1 | 8/2006 | Flaherty | 600/595 |
| 2006/0241356 A1 | 10/2006 | Flaherty | 600/301 |
| 2006/0293948 A1 | 12/2006 | Weinblatt | 705/14 |
| 2006/0294537 A1 | 12/2006 | Weinblatt | 725/10 |
| 2007/0066916 A1 | 3/2007 | De Lemos | 600/558 |
| 2007/0097234 A1 | 5/2007 | Katayama | 348/239 |
| 2007/0097319 A1 | 5/2007 | McKay et al. | 353/7 |
| 2007/0100666 A1 | 5/2007 | Stivoric et al. | 705/3 |

(56) References Cited

U.S. PATENT DOCUMENTS

| | | | |
|---|---|---|---|
| 2007/0123794 A1 | 5/2007 | Togino | 600/558 |
| 2007/0150916 A1 | 6/2007 | Begole et al. | 725/10 |
| 2007/0167690 A1 | 7/2007 | Miyazaki et al. | 600/300 |
| 2007/0260127 A1 | 11/2007 | El-Nokaly et al. | 600/301 |
| 2007/0265507 A1 | 11/2007 | de Lemos | 600/300 |
| 2007/0273611 A1 | 11/2007 | Torch | 345/8 |
| 2007/0282912 A1 | 12/2007 | Reiner | 707/104.1 |
| 2007/0287881 A1 | 12/2007 | Akimov et al. | 600/26 |
| 2007/0300174 A1 | 12/2007 | Macbeth et al. | 715/772 |
| 2008/0043013 A1 | 2/2008 | Gruttadauria et al. | 345/419 |
| 2008/0065468 A1 | 3/2008 | Berg et al. | 705/10 |
| 2008/0071136 A1 | 3/2008 | Oohashi et al. | 600/27 |
| 2008/0146890 A1 | 6/2008 | LeBoeuf et al. | 600/300 |
| 2008/0255949 A1* | 10/2008 | Genco | A61B 5/0205 705/14.4 |
| 2009/0030287 A1 | 1/2009 | Pradeep et al. | 600/300 |
| 2009/0270170 A1 | 10/2009 | Patton | 463/36 |
| 2010/0004977 A1 | 1/2010 | Marci et al. | 705/10 |
| 2010/0010317 A1 | 1/2010 | De Lemos et al. | 600/300 |
| 2010/0010370 A1 | 1/2010 | De Lemos et al. | 600/558 |
| 2010/0039618 A1 | 2/2010 | De Lemos | 351/209 |
| 2012/0237084 A1 | 9/2012 | De Lemos | 382/103 |
| 2013/0331729 A1 | 12/2013 | De Lemos et al. | 600/558 |

FOREIGN PATENT DOCUMENTS

| | | |
|---|---|---|
| JP | 11014510 | 1/1999 |
| JP | 2000-508557 | 7/2000 |
| JP | 2006-325756 | 12/2006 |
| WO | WO 90/02543 | 3/1990 |
| WO | WO 97/33515 | 9/1997 |
| WO | WO 97/38624 | 10/1997 |
| WO | WO 99/24159 | 5/1999 |
| WO | WO 03/105786 | 12/2003 |
| WO | WO 2005/032503 | 4/2005 |
| WO | WO 2005/043453 | 5/2005 |
| WO | WO 2006/111476 | 10/2006 |
| WO | WO 2007/096706 | 8/2007 |
| WO | WO 2007/102053 | 9/2007 |
| WO | WO 2008/014346 | 1/2008 |
| WO | WO 2008/023260 | 2/2008 |
| WO | WO 2008/129356 | 10/2008 |
| WO | WO 2010/004426 | 1/2010 |
| WO | WO 2010/004429 | 1/2010 |
| WO | WO 2010/018459 | 2/2010 |
| WO | WO 2010/100567 | 10/2010 |

OTHER PUBLICATIONS

Brave, Scott, et al., "Emotion in Human-Computer Interaction", Chapter in preparation for *Handbook of Human-Computer Interaction*, Department of Communication, Stanford University, [no date], 50 pages.

Cohn, Jeffrey F., et al., "Multimodal Coordination of Facial Action, Head Rotation, and Eye Motion During Spontaneous Smiles", To appear in *Proceedings of the Sixth IEEE International Conference on Automatic Face and Gesture Recognition (FG'04)* Seoul, Korea, 7 pages.

Crosby, Martha E., et al., "Physiological Data Feedback for Application in Distance Education", *ACM* 1-58113-448-7-11/14/01, PUI 2001, Orlando, Florida, copyright 2001, 5 pages.

Jackson, Daren C., et al., "Now You Feel It, Now You Don't: Frontal Brain Electrical Asymmetry and Individual Differences in Emotion Regulation", *Physiological Science*, vol. 14, No. 6, Nov. 2003, pp. 612-617.

Jacob, Robert J. K., "Eye Movement-Based Human-Computer Interaction Techniques: Toward Non-Command Interfaces", Human-Computer Interaction Lab, Naval Research Laboratory, Washington, D.C., [no date], 81 pages.

Kulic, D., et al., "Estimating Intent for Human-Robot Interaction" Department of Mechanical Engineering, University of British Columbia, [no date], 6 pages.

Lang, Peter J., "International Affective Picture System (IAPS): Instruction Manual and Affective Ratings", *Technical Report A-6*, The Center for Research in Psychophysiology, University of Florida, 2005, 56 pages.

Papert, Seymour, et al., "Computer Tracking of Eye Motions", *Artificial Intelligence Memo No. 123*, Vision Memo, Massachusetts Institute of Technology, Project MAC, Mar. 1967, 5 pages.

Schafer, Annette, "Companies Spend Billions on Marketing Campaigns, But Neuroscientists Could Someday Determine Which Ads Best Capture Consumers' Attention", *Scientific American Mind*, www.sciammind.com, [no date], pp. 72-75.

Schubert, Emery, "Emotionface: Prototype Facial Expression Display of Emotion in Music", *Proceedinqs of ICAD 04-Tenth Meeting of the International Conference on Auditory Display*, Sydney, Australia, Jul. 6-9, 2004, 1 page.

Taylor, J. G., et al., "Modelling the Interaction of Attention and Emotion", *BICS 2004*, Aug. 29-Sep. 1, 2004, Department of Mathematics, King's College, 4 pages.

Tobii Technology, Product Description, Tobii 1750 Eye-Tracker, Release B, Release Date: Nov. 2003, 16 pages.

Tobii Technology, Product Description, ClearView 2, Eye Gaze Analysis Software, Version 2.0, Sep. 2003, 16 pages.

Tobii Technology, Product Description, ClearView 2, Eye-Gaze Analysis Software (describing Release 2.1, Jan. 2004), Copyright 2003, 16 pages.

Bojko, Agnieszka, "Eye Tracking in User Experience Testing: How to Make the Most of It", *Proceedings of the UPA 2005 Conference*, 9 pages.

Yartz, Andrew R., et al., "Addressing the Specificity of Affective Startle Modulation: Fear Versus Disgust", *Biological Psychology*, vol. 59, 2002, pp. 55-68.

Duric et al., "Integrating Perceptual and Cognitive Modeling for Adaptive and Intelligent Human-Computer Interaction", *Proceedings of the IEEE*, vol. 90, No. 7, Jul. 2002, XP011065033, pp. 1272-1289.

Zhai et al., "Realization of Stress Detection Using Psychophysiological Signals for Improvement of Human-Computer Interaction", Southeastcon, 2005, *Proceedings, IEEE*, Ft. Lauderdale, Florida, Apr. 8-10, 2005, XP010789761, pp. 415-420.

Eye Tracking Portal, http://www.eye-tracking.info, three articles: 1) "ASL Launches Mobile Eye", Anonymous, Saturday, Dec. 11 [year?], the URL for this story is http://www.eye-tracking.info/modules.php?name=News&file=article&sid=3, 2 pages. 2) "RIT Takes Eye-Tracking Research to Next Level", Anonymous, Wednesday, Mar. 23 [year?], the URL for this story is http://www.eye-tracking.info/modules.php?name=News&file=article&sid=10, 2 pages. 3) "Did-it, Enquiro, and Eyetools Uncover Google?s Golden Triangle", Anonymous, Mar. 1, 2005, the URL for this story is http://www.eye-tracking.info/modules.php?name=News&file=article&sid=8, 3 pages.

Ioannou et al., "Emotion Recognition Through Facial Expression Analysis Based on a Neurofuzzy Network", *Neural Networks*, Elsevier Science Publishers, vol. 18, No. 4, May 2005, XP004965788, pp. 423-435.

Lien et al., "Detection, Tracking, and Classification of Action Units in Facial Expression", *Robotics and Autonomous Systems*, Elsevier Science Publishers, vol. 31, No. 3, May 2000, XP004197692, pp. 131-146.

Ikehara et al., "Assessing Cognitive Load with Physiological Sensors", *Proceedings of the 38th Hawaii International Conference on System Sciences*, Jan. 3, 2005, XP010762783, pp. 295A-1-295A-9.

Partala, Timo et al., "Pupil Size Variation as an Indication of Affective Processing", *International Journal of Human-Computer Studies*, vol. 59, Issues 1-2, Jul. 2003, pp. 185-198.

Nold, Christian, "Bio Mapping", Jan. 2004, www.biomapping.net. 15 pages.

Geirsson, Halldor, "Detection of Outliers", Mar. 21, 2003, hraun.vedur.is/ja/skyrslur/contgps/node1.html, 3 pages.

Alaoui-Ismaili, O. et al., "Odor Hedonics: Connection with Emotional Response Estimated by Automatic Parameters", Oxford University Press, pp. 237-248.

(56) References Cited

OTHER PUBLICATIONS

Alata, Mohanad et al., "Text Detection and Character Recognition Using Fuzzy Image Processing", *Journal of Electrical Engineering*, vol. 57, No. 5, 2006, pp. 258-267.
Campbell, Christopher et al., "A Robust Algorithm for Reading Detection", *PUI 2001*, Orlando, Florida, 7 pages.
Goldberg, Joseph et al., "Eye Tracking in Web Search Tasks: Design Implications", ETRA '02, New Orleans, Louisiana, 2002, pp. 51-58.
ISCAN Incorporated, "Magnetic Resonance Remote Eye Tracking Laboratory", Eye & Target Tracking Instrumentation, 2000, 2 pages.
ISCAN Incorporated, "ETL-300 Binocular Free-Head Eye Tracking Laboratory", Eye & Target Tracking Instrumentation, 2000, 4 pages.
ISCAN Incorporated, "ETL-400 Tabletop Remote Eye Tracking Laboratory", Eye & Target Tracking Instrumentation, 2000, 4 pages.
ISCAN Incorporated, "ETL-500 Head-Mounted Eye Tracking Laboratory", Eye & Target Tracking Instrumentation, 2000, 4 pages.
Niemic, Christopher et al., "Studies of Emotion, A Theoretical and Emperical Review of Psychophysiological Studies of Emotion", jur.rochester.edu, vol. 1, Issue 1, Fall 2002, pp. 15-18.
Pan, Bing et al., "The Determinants of Web Page Viewing Behavior: An Eye-Tracking Study", Association for Computing Machinery, Inc., 2004, pp. 147-154.
Rupp, Heather et al., "Sex Differences in Viewing Sexual Stimuli: An Eye-Tracking Study in Men and Women", *Hormones and Behavior*, vol. 51, 2007, pp. 524-533.
Schnipke, Susan et al., "Trials and Tribulations of Using an Eye-Tracking System", CHI 2000, Apr. 1-6, 2000, pp. 273-274.
Spillers, Frank, Demystifying Usability: Eye-Tracking Studies—Usability Holy Grail?, http://experiencedynamics.blogs.com/site_search_usability/2004/12/eyetracking_stu.html, printed Dec. 7, 2007, 10 pages.
Wilhelm et al., "Affective Computing: Using Computational Intelligence Techniques to Classify the Psychophysiological Signatures of Fearful, Sad, and Calm Affective States", 1 page.
Visual Impact Test—Eye Tracking—Emotional Response—Visual Attention—Eyetracking, Black Box Global Research, printed from http://blackboxglobal.com/visual-impact.html, printed Dec. 7, 2007, 3 pages.
Brave et al., The Human-Computer Interaction Handbook, 2002, pp. 87-88.
Geirsson et al., "Continuous GPS Measurements in Iceland 1999-2002", published Mar. 2003, Chapter 3.2 "Detection of Outliers", 92 pages.
Ebrahimi, Touradj et al., "Brain-Computer Interface in Multimedia Communication", *IEEE Signal Processing Magazine*, Jan. 2003, IEEE Press, USA, pp. 14-24.
Hayashi, Hidehiko, et al., "Eye Movement Tracking to Support the Second Language Learners' Self-Learning in Comprehension of English Texts", *2002 IEEE International Conference on Systems, Man and Cybernetics*, vol. 7, Oct. 9, 2002, XP-002562615, 6 pages.
Brosch, Tobias, et al., "The Perception and Categorisation of Emotional Stimuli: A Review", *Cognition and Emotion*, vol. 24, No. 3, Jan. 1, 2010, pp. 377-400.
European Patent Application No. 06849514.2—Communication Pursuant to Article 94(3) EPC mailed Jul. 10, 2008, 6 pages.
European Patent Application No. 06849514.2—Response to Communication Pursuant to Article 94(3) EPC filed Jan. 13, 2009, 21 pages.
European Patent Application No. 06849514.2—Summons to Attend Oral Proceedings Pursuant to Rule 115(1) EPC mailed Jul. 21, 2009, 31 pages.
European Patent Application No. 06849514.2—Written Submissions filed Oct. 13, 2009, 26 pages.
European Patent Application No. 06849514.2—Provision of the Minutes in Accordance with Rule 124(4) EPC mailed Jul. 19, 2010, 8 pages.
European Patent Application No. 06849514.2—Decision to Refuse a European Patent Application mailed Jul. 19, 2010, 40 pages.
Bradley, Margaret M., et al., "The Pupil as a Measure of Emotional Arousal and Autonomic Activation", *Psychophysiology*, vol. 45, available online Feb. 12, 2008, pp. 602-607.
International Search Report and Written Opinion mailed Feb. 3, 2010 in International Application No. PCT/IB2009/006756, 14 pages.
Reply to Written Opinion filed Jun. 14, 2010 in International Application No. PCT/IB2009/006756, 4 pages.
International Preliminary Report on Patentability mailed Nov. 16, 2010 in International Application No. PCT/IB2009/006756, 6 pages.
International Search Report and Written Opinion mailed Dec. 16, 2009 in International Application No. PCT/IB2009/006528, 14 pages.
Amendments Under Article 19 filed Feb. 12, 2010 in International Application No. PCT/IB2009/006528, 12 pages.
Reply to Written Opinion filed May 6, 2010 in International Application No. PCT/IB2009/006528, 15 pages.
International Preliminary Report on Patentability mailed Oct. 14, 2010 in International Application No. PCT/IB2009/006528, 12 pages.
Wiley Online Library page for: "The Pupil as a Measure of Emotional Arousal and Automatic Activation", Wiley Online Library, http://onlinelibrary.wiley.com/doi/10.1111/j.1469-8986.2008.00654.x/abstract, available online Dec. 5, 2011, pp. 1-3.

* cited by examiner

Male respondents: BlackCherry, Chocolate, Coconut and Orange.

Male respondents: Animalic, Fish, RomanoCheese and Seaweed.

SYSTEM AND METHOD FOR DETERMINING EMOTIONAL RESPONSE TO OLFACTORY STIMULI

CROSS-REFERENCE TO RELATED APPLICATIONS

This application is the U.S. National Stage of PCT/IB2010/000821, filed Mar. 5, 2010, which in turn claims the benefit of U.S. Provisional Patent Application Ser. No. 61/158,197, entitled "SYSTEM AND METHOD FOR DETERMINING EMOTIONAL RESPONSE TO OLFACTORY STIMULI", filed Mar. 6, 2009. The content of both applications are hereby incorporated herein by reference in their entirety.

FIELD OF THE INVENTION

The invention relates to a system and method for determining the instinctual and other emotional responses to of olfactory stimuli.

BACKGROUND OF THE INVENTION

It is well known that aromas in food and other products can impact a person's perception of (or reaction to) such products. However, to date, it has been difficult to obtain a quantitative measurement of a person's response to an aroma.

One of the most common ways to test human response to aroma has been to form a group of test subjects, who are trained for months to be able to learn how to distinguish between various aromas. Once trained, the subjects may provide subjective responses to aromatic tests. This method is costly, inefficient, and may provide subjective results.

It is known that consumer purchasing activity can include an emotional component. Until recently, it has been difficult to determine a person's emotional response to a stimulus. Recently, however, the assignee of the present application has developed a system for determining emotional response to stimuli (e.g., primarily visual stimuli). A commercial implementation of an emotional response measuring system has been released by the assignee and is known as The Emotion Tool®. Examples of aspects of the Emotion Tool are disclosed in U.S. patent application Ser. No. 11/522,476, filed Sep. 18, 2006; U.S. patent application Ser. No. 11/685,552, filed Mar. 13, 2007; U.S. patent application Ser. No. 12/170,059, filed Jul. 9, 2008; and U.S. patent application Ser. No. 12/170,041, filed Jul. 9, 2008, each which are hereby incorporated herein by reference in their entirety. In one implementation, the system includes an eye tracking device to measure eye data (e.g., eye position/movement data, blink data, and pupil dilation) sampled at a predetermined sampling rate (e.g., 50, 60, 120, and/or other samples per second) regarding a subject's response to a predetermined stimulus (e.g., a slide or other graphic displayed on a computer monitor). The Emotion Tool® receives the raw eye data from the eye tracking device, and processes and analyzes the raw eye data to determine a person's emotional response to the visual stimulus. Significantly, the emotional response can include a pre-cognitive (or instinctual) component and a cognitive (or rational) emotional component. The instinctual emotional response component may relate to a portion of the emotional response that is induced by the limbic system, including the amygdala portion of the brain (as opposed to portions of the body that control cognitive response).

The Emotion Tool® described in these applications may be used in connection with measuring emotional response of olfactory stimuli. However, the applicant has determined that some aspects of emotional response testing based on olfactory stimuli present certain potential problems and design considerations that are not necessarily present with visual stimuli. As a result, the applicant has found that some drawbacks would result if the Emotion Tool® was used for emotional response testing based on olfactory stimuli. The applicant has found that these drawbacks, if not addressed, may adversely impact the validity and/or value of the test results for olfactory stimuli.

For example, test results may vary depending on whether a person is in an inhalation or exhalation portion of a respiratory cycle when they are exposed to the olfactory stimuli.

Additionally, the distance between a person's nose and a nozzle of an olfactory stimulus dispenser may vary depending on, among other things, the person's head position. If this is not taken into account, this may lead to flawed test results.

Moreover, variations in flow rate of an olfactory stimulus can occur. If this is not taken into account, this may lead to flawed test results.

Further, if certain aspects of the olfactory components of the environment vary from one test to another, this may lead to flawed test results.

These and other drawbacks exist with known systems and methods for testing associated with olfactory stimuli.

SUMMARY OF THE INVENTION

The invention addressing these and other drawbacks relates to a system and method for determining pre-cognitive and/or cognitive emotional response to predetermined olfactory stimuli. Among other things, the invention may include exposing a test subject, during a test, to a controlled flow of a predetermined olfactory stimulus, measuring eye data (e.g., using an eye tracking device) corresponding to when the olfactory stimulus reached the subject's nose, and analyzing and processing the eye data for determining the subject's emotional response to the olfactory stimulus.

Olfactory stimuli refer to stimuli that stimulate the olfactory system of a test subject and may include aromas, scents, fragrances, odors and/or other olfactory stimuli. It should be noted that those having skill in the art will recognize that various chemical substances may be utilized as to produce olfactory stimuli and therefore that aromas, scents, fragrances odors, and/or other olfactory stimuli may be produced using one or more chemical substances. It is known that at least a portion of the taste experience impacts the olfactory sensory perception. According to one aspect of the invention, if desired, taste stimuli may at least in part be used to create the olfactory stimuli. In other words, the olfactory stimuli may include a taste component.

It should be noted that, for ease of explanation, various aspects of the invention are described in terms of aroma, which is an example of an olfactory stimulus. The recitations of aroma throughout the application are exemplary and, unless so indicated, should not be viewed as limiting. Other olfactory stimuli may also be used without departing from the scope of the invention.

Also, while various aspects of the invention relate to one or more test subjects participating in a test, it should be recognized that test subjects may include subjects that are exposed to olfactory and/or other stimuli while not actively and/or knowingly participating in a test. For example, the invention may be used at a cinema hall (or other location) to induce an emotional response in a subject by exposing the subject to olfactory and/or other stimuli (in which case the subject is not actively participating in a test). As such, the recitations of test subjects throughout the application should not be viewed as limiting, unless so indicated.

In some implementations, the system may include one or more of: a controllable olfactory stimuli dispenser for dispensing/releasing a predetermined olfactory stimulus; an olfactory stimuli flow detector for detecting a flow rate of the released olfactory stimulus; a distance detection device for measuring the distance from the olfactory stimuli dispenser to a test subject, a respiratory measuring device for measuring respiratory cycle information of test subjects; an environmental sensor for measuring various environmental parameters; an eye tracking device for measuring eye data (e.g., eye position/movement, blink data and/or pupil dilation); an emotional response measuring system for analyzing and processing eye data to determine the subject's emotional response to olfactory, visual, and/or other stimuli; a computer application with various software modules; and/or other components. In some implementations, the computer application may include a test management module, a respiration signal analysis module, an olfactory stimuli control module, a visual/other stimulus control module, a response data collection module, a reporting module, and/or other modules.

In some implementations, the controllable olfactory stimuli dispenser may dispense/release one or more predetermined olfactory stimuli such as, for example, aromas. The controllable olfactory stimuli dispenser may include one or more aroma sources containing an aroma supply of similar and/or different aromas. The controllable olfactory stimuli dispenser, upon receiving a control signal to release or dispense a desired aroma, may select an aroma source associated with the desired aroma and dispense the desired aroma from the aroma source. In some implementations, aromas from different aroma sources may be combined to generate the desired aroma, and the controllable olfactory stimuli dispenser may select more than one aroma source to generate and/or dispense the desired aroma. In some implementations, the olfactory stimuli dispenser may mix the aromas (in desired and/or pre-determined concentrations) from the selected aroma sources to generate the desired aroma. In some implementations, a nozzle may be attached to the controllable olfactory stimuli dispenser via which the dispensed aroma is directed towards the test subject.

In some implementations, an olfactory stimuli flow detector may be coupled and/or attached to the controllable olfactory stimuli dispenser and may detect flow parameters such as the flow rate of the aroma released from the olfactory stimuli dispenser and/or other flow parameters. The olfactory stimuli flow detector may detect the flow rate of the aroma and the time the aroma was released by the olfactory stimuli dispenser, for example, to estimate the arrival time at the test subject's nose (e.g., given a known distance from the dispenser outlet to the test subject's nose).

In some implementations, a distance detection device may measure a distance between the olfactory stimuli dispenser and a test subject. In some instances, the distance detection device may measure the distance from the nozzle of the olfactory stimuli dispenser to the nose of the test subject. In some implementations, based on the distance measurement and the flow rate detected by the olfactory stimuli flow detector, the time at which an aroma actually reached a subject's nose can be determined.

In some implementations, a respiratory measuring device may measure respiratory cycle information of test subjects. The respiratory measuring device may measure the amplitude, timing, pattern, volume, velocity, intensity, frequency, and/or other respiration parameters.

In some implementations, an environmental sensor may measure various environmental parameters relevant to the invention such as, for example, temperature, humidity, olfactory aspects, and/or other environmental parameters. In some instances, various environmental conditions may be monitored and/or controlled to reduce the impact of olfactory and/or other aspects of environmental conditions.

In some implementations, an eye tracking device may comprise a camera or other known or future-developed device and/or sensor that measures various eye properties of subjects (e.g., while the test subject is being exposed to one or more olfactory, visual, and/or other stimuli). Examples of eye properties that may be measured may include blink rate, eye movement, pupil dilation, gaze information, eye ball temperature, eye color, and/or other properties.

In some implementations, a system for determining pre-cognitive and/or cognitive emotional response to predetermined olfactory stimuli may include a computer application. In some implementations, the computer application may comprise or include one or more software modules including: a test management module, a respiration signal analysis module, an olfactory stimuli control module, a visual/other stimulus control module, a response data collection module, a reporting module, and/or other modules.

The test management module may comprise one or more sub-modules for managing the setup of tests for various test subjects, performing calibration and/or pre-testing functions, administering the tests to test subjects, and/or performing other functions. Other modules of the computer application may also include sub-modules for performing various features and functions.

The respiration signal analysis module may obtain respiratory cycle information from the respiratory measuring device. From the respiratory cycle information, the respiration signal analysis module may determine a respiration pattern of the test subject. The respiration pattern may include inhalation and exhalation portions of the test subject's respiration cycle. In some implementations, the respiration signal analysis module may determine and/or predict a next inhalation portion of the test subject's respiration cycle such that the release of the olfactory and/or other stimulus may be timed to be in synchronization with the inhalation portion of the test subject's respiration cycle. In some implementations, the olfactory stimuli may be released at or near the beginning of the inhalation portion. This may ensure that different test subjects (across different tests and/or different stimuli) are exposed to the olfactory and/or other stimuli at approximately the same time during an inhalation cycle. Having substantially identical olfactory stimuli exposure conditions for the different test subjects may ensure accurate emotional response determination.

The olfactory stimuli control module may comprise one or more sub-modules for controlling the release of olfactory stimuli (e.g., in synchronization with the respiratory cycle of a test subject, as measured/detected by the respiration signal analysis module), analyzing the properties of the olfactory stimuli and/or olfactory stimuli dispenser, purging the olfactory stimuli residue from the environment, and/or performing other functions.

An olfactory stimuli properties analysis sub-module may determine olfactory stimuli and/or olfactory stimuli dispenser properties. In some implementations, the olfactory stimuli properties sub-module may determine aroma and/or olfactory stimuli dispenser properties prior to aroma release such as, for example, aroma source(s) to be selected for a test, a relative volume of aroma to be dispensed from aroma source(s), molecular properties of aromas in aroma source(s), a desired flow rate at which aroma is to be dispensed from aroma source(s), the time of release, and/or other properties. In some implementations, one or more of the aroma and/or olfactory stimuli dispenser properties may be fixed for each test. In some implementations, one or more of the aroma and/or olfactory stimuli dispenser properties (e.g., relative volume of aroma to be dispensed from aroma source(s), desired flow rate at which aroma is to be dispensed from aroma source(s), etc.) may be modified based on the distance measured from the olfactory stimuli dispenser to the test subject by the distance detection device. For instance, if a test subject is seated relatively far away from the nozzle, the flow rate at which aroma is dispensed from aroma source(s) may be higher than that for a test subject who is seated relatively closer to the nozzle. This may be used to ensure that the intensity at which the test subjects are impacted with the olfactory stimuli remains substantially identical across different tests and/or different test subjects, and/or different stimuli.

In some implementations, the olfactory stimuli properties analysis sub-module may determine aroma and/or olfactory stimuli dispenser properties at and/or after aroma release. In some implementations, olfactory stimuli properties analysis sub-module may receive aroma flow rate information detected by the olfactory stimuli flow detector when the aroma is released by the olfactory stimuli dispenser. By analyzing the flow rate information, the olfactory stimuli properties analysis sub-module may determine whether the aroma was actually released by the olfactory stimuli dispenser, whether the aroma was released at the desired flow rate, and/or may determine other aroma and/or olfactory stimuli dispenser properties. For instance, if a determination was made that aroma was not released and/or released at a lower flow rate than desired flow rate by the olfactory stimuli dispenser, this may indicate that the olfactory stimuli dispenser and/or aroma source(s) may be contaminated.

An olfactory stimuli release control sub-module may determine a time at which the olfactory stimuli should be triggered for release to reach the subject's nose at a predetermined time. The olfactory stimuli release control sub-module may also generate a control signal (for the controllable olfactory stimuli dispenser) to release the olfactory stimuli at the determined time. In some implementations, the time for release may be determined based on respiratory cycle information. For example, the olfactory stimuli release control module may receive respiratory cycle information from the respiration signal analysis module, and may generate a control signal to release the olfactory stimuli in relative synchronization with the test subject's respiration pattern (or otherwise as desired). Such controlled release enabled specific control of (and thus, modulation of) delivery of olfactory stimuli to test subjects as well as synchronized/normalized delivery of olfactory stimuli across multiple test subjects, which may render test results more meaningful/useful.

In some implementations, the predetermined time may correspond to an inhalation portion of the test subject's respiration cycle or other respiration parameters (or to a projected time at which the test subject will be in an inhalation portion of the respiration cycle when the olfactory stimuli is at/near the subjects nose/mouth). Based, at least in part, on respiration cycle/pattern information received from the respiration signal analysis module, the olfactory stimuli release control sub-module may generate a control signal to release the olfactory stimuli at the determined time, such that the olfactory stimuli reaches the subject's nose at a time and/or time period when the subject is in the inhalation portion of the respiration cycle. In some implementations, the olfactory stimuli release control sub-module may generate the control signal to release the olfactory stimuli at or near the beginning of the inhalation portion.

In some implementations, the timing of the olfactory stimulus release may be based on various timing parameters including for example, the distance from the nozzle of the olfactory stimuli dispenser to the subject's nose, the desired flow rate of the olfactory stimulus to be released from the olfactory stimuli dispenser, and/or other timing parameters. Based on the distance measurement from the distance detection device and the desired flow rate information from the olfactory stimuli properties analysis sub-module, the olfactory stimuli release control sub-module may determine the time at which the olfactory stimulus should be triggered for release to reach the subject's nose at a predetermined time.

In some implementations, the control signal generated by the olfactory stimuli release control module may identify one or more aroma sources from which olfactory stimuli is to be dispensed, the desired flow rate at which the olfactory stimuli is to be dispensed, and/or other information.

An olfactory stimuli purging sub-module may receive environmental parameters measured by the environment sensor. In some implementations, the olfactory stimuli purging sub-module may detect, in between stimuli and/or in between tests, environmental contamination due to olfactory residue in the olfactory stimuli dispenser, in the air around the olfactory stimuli dispenser/subject, and/or from other sources. For example, in some implementations, the olfactory stimuli purging sub-module may detect, prior to, during, and/or after the emotional response test, environmental contamination due to the olfactory residue. In some implementations, in response to such determination, the olfactory stimuli purging sub-module may control a neutralizing air generator that generates a chemical and/or pure air to neutralize/purge the olfactory residue. In some implementations, a network of neutralizing air generators may be provided. In some implementations, each of the generators may be individually and/or selectively controlled. In some implementations, some and/or all of the generators may be simultaneously controlled.

In some implementations, the olfactory stimuli release control sub-module may receive a signal from the olfactory stimuli purging module indicating environmental contamination, and in response thereto, the olfactory stimuli release control sub-module may not generate a control signal to release the olfactory stimuli because the release of olfactory stimuli may generate flawed results.

In some implementations, an emotional response measuring system may determine the subject's emotional response to olfactory, visual, and/or other stimuli. The emotional response measuring system may include an emotional response determination module, and/or other modules.

In some implementations, the emotional response determination module may determine information regarding the test subject's emotional response to the stimuli from the eye data measured by the eye tracking device.

In some implementations, the distance detection device and the respiratory measuring device may continue to measure the distance between the nozzle of the olfactory stimuli dispenser and the subject's nose and the respiratory cycle information of the test subject after the release of the olfactory stimulus. Based on the distance data and the aroma flow information measured by the olfactory stimuli flow detector at the time of aroma release, the time at which the aroma actually reached the subject's nose (i.e., actually impacted the subject) may be determined. This data may be used to assess whether the distance varied from the time the olfactory stimuli was released to the time the olfactory stimulus actually impacted the subject, whether the respiration varied from the time the olfactory stimuli was released to the time the olfactory stimulus actually impacted the subject, whether the flow rate at which the olfactory stimuli was released from the olfactory stimuli dispenser varied from the desired flow rate, and/or other variations.

In some implementations, because the time at which olfactory stimuli actually impacted the test subject may be determined as described above, the corresponding measured eye data may be analyzed by the emotional response determination module to determine the test subject's emotional response to the olfactory stimuli. For example, in some instances, knowledge of measured emotional response indicators occurring after the known arrival time of an olfactory stimulus at a subject's nose may be utilized in determining an emotional response. Because the test subject may be presented with visual stimuli and olfactory stimuli during a given test, the subject's emotional response to the olfactory stimuli and the subject's emotional response to the visual and/or other stimuli may also be parsed/determined.

In some implementations, the distance detection device may continue to measure the distance between the nozzle of the olfactory stimuli dispenser and the subject's nose at and/or after it has been determined that the olfactory stimuli has reached the subjects nose and/or that the subject has detected the aroma. In some instances, this data may be utilized, at least in part, to determine/measure an emotional response to the olfactory stimuli. For example, any variance in the distance between the nozzle of the olfactory stimuli dispenser and the subject's nose may be an indicator of a precognitive and/or cognitive emotional response (e.g., the subject has either instinctually or rationally recoiled from or moved towards the olfactory stimuli). In some implementations, other parameters/measurements may be made at and/or after it has been determined that the olfactory stimuli has reached the subjects nose and/or that the subject has detected the aroma.

In some implementations, the invention may include a method for determining a distance from the subject's nose to a nozzle of an olfactory stimuli dispenser and/or analyzing the test subject's respiration cycle (ideally to determine a respiration pattern), and controllably releasing an olfactory stimulus to ideally reach the subject's nose at a predetermined time, taking into account the determined distance and/or the respiration pattern. As discussed above in relation to various system components, these features enable specific control of (and thus, modulation of) delivery of olfactory stimuli to test subjects as well as synchronized/normalized delivery of olfactory stimuli across multiple test subjects, which may render test results more meaningful/useful. In some instances, the predetermined time may correspond to an inhalation portion of the test subject's respiration cycle or to a projected time at which the subject will be in an inhalation portion of the respiration cycle.

In some implementations, controllably releasing an olfactory stimulus may be timed, ideally, to be in synchronization with an inhalation portion of the test subject's respiration cycle. In some implementations, the timing of the stimulus release may be based on various timing parameters including for example, the distance from the nozzle to the nose, a desired flow rate of the olfactory stimulus to be released from the olfactory stimuli dispenser, and/or other parameters.

In some implementations, controllably releasing an olfactory stimulus may be timed to be in synchronization with the release of other olfactory or non-olfactory stimuli, other sensory inputs (for example, facial expression), test subject's gaze data and/or other parameters. For example, in a scenario where the test subject is in a supermarket and is looking at a certain product, the test subject's gaze data may be utilized to control the release of an aroma associated with the product.

According to one example, based on a desired flow rate of the olfactory stimuli, the distance from the nozzle of the olfactory stimuli dispenser to the subject's nose, and the respiration cycle/pattern information, a time at which the olfactory stimulus should be triggered for release to reach the subject's nose at a predetermined time may be determined. A control signal to release the olfactory stimulus may be generated at the determined time, such that the olfactory stimuli reaches the subject's nose at a time and/or time period when the test subject is in the inhalation portion of the respiration cycle.

In some implementations, exposure of the test subject to visual and/or other stimuli may be timed to be in synchronization with the release of the olfactory stimuli. For example, based on the respiration cycle/pattern information (and/or distance or flow rate information), a time for release for each of olfactory, visual, and/or other stimuli may be determined, such that each of these stimuli impact the test subject at approximately the same time (for example, at a time and/or time period when the test subject is in the inhalation portion of the respiration cycle). For example, if both an olfactory and a visual stimulus are to be presented to the test subject, the exposure of the visual stimulus may be delayed because the olfactory stimulus may take some time to reach the test subject's nose.

In some implementations, subject's eye data in response to the olfactory, visual, and/or other stimulus may be measured by eye tracking device and the subject's emotional response to the olfactory, visual, and/or other stimulus may be determined by the emotional response determination module. The time at which it is determined that an olfactory stimulus actually reached, or was otherwise detected by, a subject may be taken into account when determining an emotional response of the subject using measured emotional response data.

In some implementations, various environmental conditions may be monitored and/or controlled to reduce the impact of olfactory and/or other aspects of environmental conditions. For example, pure air canisters may be used to purge olfactory residue from a prior test that may be in the olfactory stimuli dispenser and/or the air around the olfactory stimuli dispenser/subject. Other environmental conditions may also be controlled, for example, temperature, or humidity, among others.

Various other objects, features, and advantages of the invention will be apparent through the detailed description and the drawings attached hereto. It is also to be understood that both the foregoing general description and the following detailed description are exemplary and not restrictive of the scope of the invention.

DETAILED DESCRIPTION OF THE INVENTION

Figure 1:
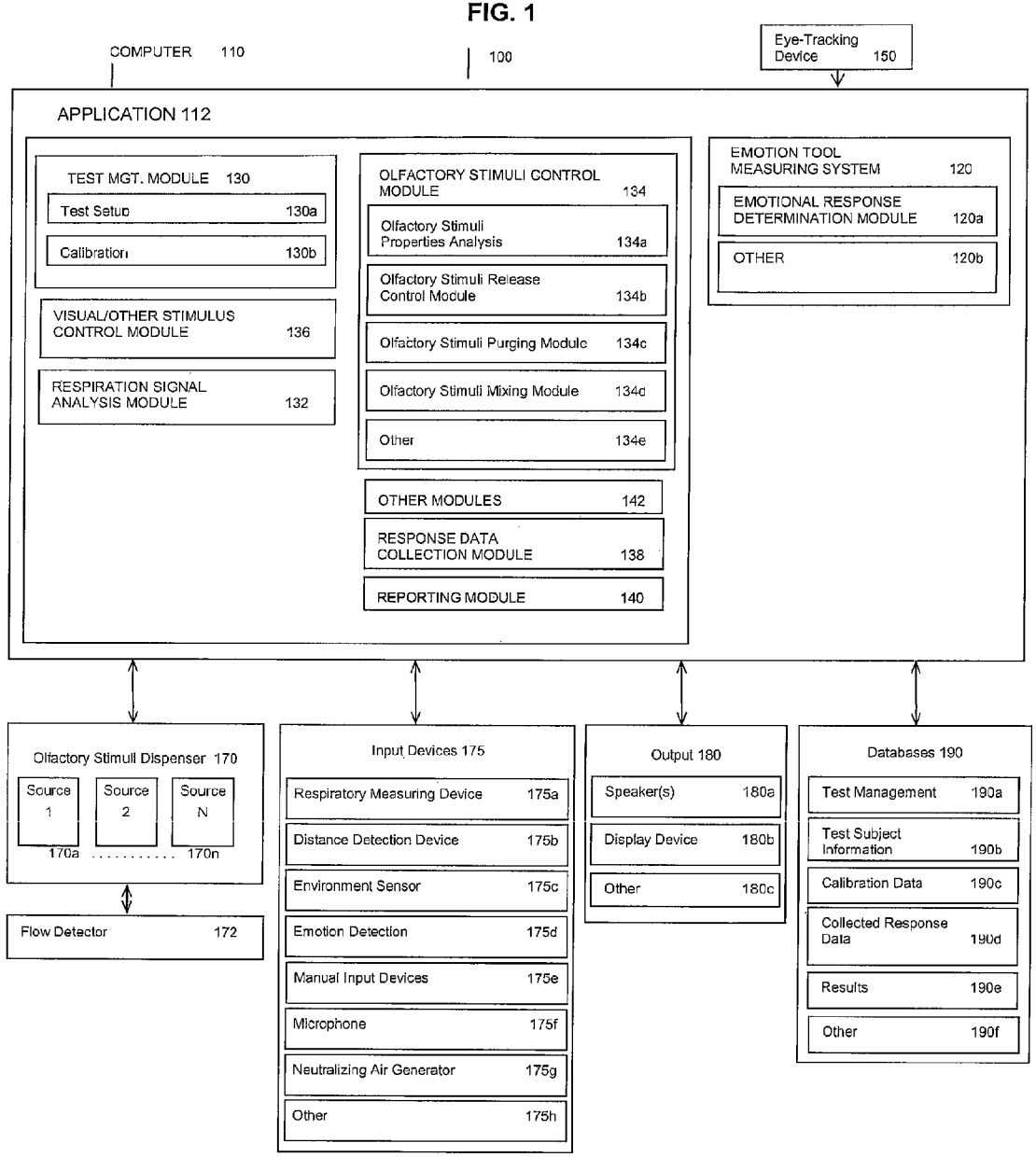
FIG. 1 illustrates an exemplary system for determining emotional response to olfactory stimuli, according to various aspects of the invention.

FIG. 1 illustrates an exemplary system 100 for determining emotional response to olfactory stimuli, according to various aspects of the invention. System 100 may include at least one computer 110 coupled to/interfaced with an eye tracking device 150, a controllable olfactory stimuli dispenser 170, one or more input devices 175, one or more output devices 180, one or more databases 190, and/or other components. Computer 110 may include a processor, circuitry and/or other hardware operable to execute computer-readable instructions. According to one aspect of the invention, computer 110 may include one or more computer-readable storage media configured to store one or more software modules, wherein the software modules include computer-readable instructions that when executed by the processor perform the features and functions described herein and/or other features and functions.

In some implementations, eye tracking device 150 may include a camera or another known or future-developed device and/or sensor configured to measure various eye properties of subjects (e.g., while the test subject is being presented with one or more olfactory, visual, and/or other stimuli). Examples of eye properties that may be measured can include blink rate, eye movement, pupil dilation, gaze information, eye ball temperature, or eye color, among others. In some implementations, eye tracking device 150 may be attached to a display device 180b, integrated with a display device 180b, or configured as a stand-alone device. Eye tracking device 150 may interface with computer 110 via any suitable connection or interface.

In some implementations, a controllable olfactory stimuli dispenser 170 may dispense/release a predetermined olfactory stimulus, for example an aroma. The controllable olfactory stimuli dispenser 170 may include one or more aroma sources 170a, . . . , 170n, containing an aroma supply of similar and/or different aromas. The controllable olfactory stimuli dispenser 170, upon receiving a control signal to release or dispense a desired aroma, may select an aroma source associated with the desired aroma and dispense the desired aroma from the aroma source. In some implementations, aromas from different aroma sources may be combined to generate the desired aroma, and the controllable olfactory stimuli dispenser 170 may select more than one aroma source to generate and/or dispense the desired aroma. In some implementations, the olfactory stimuli dispenser 170 may mix the aromas (in desired and/or pre-determined concentrations) from the selected aroma sources to generate the desired aroma. In some implementations, a nozzle may be attached to the controllable olfactory stimuli dispenser 170 via which the dispensed aroma is directed towards the test subject.

In some implementations, an olfactory stimuli flow detector 172 may be coupled and/or attached to the controllable olfactory stimuli dispenser 170 and may detect flow parameters such as, for example, the flow rate of the aroma released from the olfactory stimuli dispenser 170 and/or other flow parameters. The olfactory stimuli flow detector 172 may detect the flow rate of the aroma and the time the aroma was released by the olfactory stimuli dispenser 170. This may be done, for example, to estimate the arrival time at the test subject's nose (e.g., given a known distance from the dispenser outlet to the test subject's nose). The olfactory stimuli flow detector may comprise, for example, a thermal sensor, gas sensor, pressure sensor, or any other sensor or future developed sensor that can detect the flow rate of the aroma at the time the aroma was released by the olfactory stimuli dispenser 170.

In some implementations, one or more input device(s) 175 may comprise one or more of a respiratory measuring device 175a, a distance detection device 175b, an environment sensor 175c, an emotion detection sensor 175d, a manual input device 175e, a microphone 175f, a neutralizing air generator 175g and/or other input devices 175h.

In some implementations, respiratory measuring device 175a may measure respiratory cycle information of test subjects. Respiratory measuring device 175a may measure the amplitude, timing, pattern, volume, velocity, intensity, frequency, and/or other respiration parameters. Respiratory measuring device 175a may include, for example, a stretch sensitive sensor attached to a torso of a test subject, a thermal sensor (optic sensor), a LIDAR sensor, a $CO_2$ sensor, an airflow sensor, a humidity sensor, a gas sensor, or any other sensor or future developed sensor that can measure respiratory cycle information of test subjects.

In some implementations, distance detection device 175b may measure a distance from the olfactory stimuli dispenser 170 to a test subject. Distance detection device 175b may measure, inter alia, the distance from the nozzle of the olfactory stimuli dispenser 170 to the nose of the test subject.

In some implementations, distance detection device 175b may measure a distance from display device 180b and/or eye tracking device 150 to a test subject. In some implementations, eye tracking device 150 may itself operate as a distance detection device to measure the distance from the eye tracking device 150 to the test subject. In some implementations, the position of the nozzle of olfactory stimuli dispenser 170 may be fixed relative to eye tracking device 150. Thus, the distance between the test subject's head and eye tracking device 150 may be linearly proportional to the distance between the subject's head/nose and the nozzle. As such, the distance between eye tracking device 150 to the test subject (in combination with position information regarding eye tracking device 150 and the nozzle) may provide sufficient information to calculate the distance between the nozzle of olfactory stimuli dispenser 170 and the nose of the test subject.

In some implementations, two distance detection sensors 175b may be provided, one to measure the distance from olfactory stimuli dispenser 170 to a test subject, and the other to measure the distance from display device 180b and/or eye tracking device 150 to a test subject. Distance detection device 175b may comprise, for example, radars, optic sensors, camera, laser devices, sound sensors, thermal sensor (optic sensor), LIDAR sensor, and/or any other sensor or future developed sensor that can perform the distance measurement.

In some implementations, environmental sensor 175c may measure various environmental parameters, for example, temperature, humidity, olfactory aspects, and/or other environmental parameters. Various environmental conditions may be monitored and/or controlled to reduce the impact of olfactory and/or other aspects of environmental conditions. Environment sensor 175c may comprise, for example, a thermal sensor, a humidity sensor, a gas sensor, or any other sensor or future developed sensor that can measure various environmental parameters.

In some implementations, emotion detection sensor 175d may comprise, for example, physiological sensors such as galvanic skin response sensors, facial recognition sensors, heart rate sensors, sweat detection sensors, stress sensors, or any other sensors or future-developed sensors that can detect physiological responses from one or more test subjects.

In some implementations, manual input device(s) 175e may include one or more of a keyboard, a mouse, or another input device that enables subjects or other persons to manually input information to the computer 110.

In some implementations, one or more microphones 175f may comprise, for example, any suitable device that enables test subjects or other persons to provide voice-activated input for responding to various instructions and messages, stimuli, and/or other information.

In some implementations, neutralizing air generator 175g may generate and/or dispense a chemical and/or pure air to neutralize and/or purge olfactory residue in olfactory stimuli dispenser 170 and/or in the air around the olfactory stimuli dispenser/subject. In some implementations, neutralizing air generator 175g may include one or more pure air canisters that may release pure air to neutralize and/or purge olfactory residue that may be in the olfactory stimuli dispenser 170 and/or the air around the olfactory stimuli dispenser/subject.

In some implementations, one or more output device(s) 180 may include a speaker 180a, one or more display device(s) 180b, and/or other output devices 180c. In one implementation, speaker 180a may include one or more speakers for audibly reproducing audio instructions, messages, stimuli, and/or other information to test subjects. One or more display device(s) 180b may include one or more monitors, Cathode Ray Tube (CRT) displays, digital flat panel displays (e.g. LCD displays, plasma displays, etc.), or other display devices for presenting visual instructions, messages, stimuli, and/or other information to test subjects.

In some implementations, databases 190 may comprise a test management database 190a, a test subject information database 190b, a calibration data database 190c, collected response data database 190d, a results database 190e, and/or other databases 190f.

Test management database 190a may store one or more tests comprising any individual, series, or combination of test stimuli that may be presented to a test subject during an emotional response test. The test stimuli presented to the test subjects may comprise any fixed or dynamic stimulus or stimuli relating to one or more of the subject's five senses (i.e., sight, sound, smell, taste, touch). The stimulus may comprise any real stimulus, or any analog or electronic stimulus that can be presented to the subject via known or future-developed technology.

In some implementations, test management database 190a may store stimuli presentation properties. For example, for a given test, test management database 190a may store one or more of a duration of presentation for one or more stimuli associated with the given test, the order of presentation for the one or more stimuli associated with the given test, whether any stimuli should be simultaneously presented, and/or other stimuli presentation properties.

In some implementations, test management database 190a may store one or more visual and/or other stimuli associated with one or more tests. In some implementations, additional visual and/or other stimuli that may not necessarily be associated with an emotional response test may also be stored in the test management database. For example, visual stimuli may include, but are not limited to, pictures, artwork, charts, graphs, text, movies, multimedia or interactive content, or other visual stimuli.

In some implementations, one or more olfactory stimuli (for example, aromas) may be associated with one or more tests, and test management database 190a may store additional information relating to properties/parameters associated with the olfactory stimuli and/or olfactory stimuli dispenser 170. For example, for a given test that requires a test subject to be exposed to an aroma the following may be stored in test management database 190a: a desired flow rate at which the aroma should be released from the olfactory stimuli dispenser 170, aroma source(s) to be selected to generate the aroma associated with the test, the concentration of each of the aromas that are to be mixed to generate the aroma associated with the test, As can be appreciated, other properties/parameters associated with the aroma and/or olfactory stimuli dispenser may also be stored in the test management database 190a. In some implementations, information relating to properties/parameters associated with one or more aromas that may not necessarily be associated with a test may also be stored in test management database 190a.

In some implementations, output presentation properties, for example, output presentation format, amount of information to be presented, and/or other output presentation properties may also be stored in test management database 190a.

In some implementations, information regarding test subjects may be stored in test subject information database 190b. Various profile information regarding the test subject including, but not limited to, name, age, gender, and/or other profile information may be stored in test subject information database 190b.

In some implementations, various calibration data associated with the system 100 and/or the test subject may be stored in calibration database 190c, as described in further detail below.

In some implementations, eye data tracked/measured by eye tracking device 150 in response to the presentation of one or more visual, olfactory, and/or other stimuli to test subjects may be stored in collected response data database 190d. Other physiological data regarding the subject's response to stimuli (for example, from the emotion detection sensor 175d) may also be stored in collected response data database 190d.

In some implementations, information regarding the analysis of the eye data and the determined emotional response of the test subject in response to the stimuli presented during the tests may be stored in results database 190e.

In some implementations, an application 112 may execute on computer 110. The application 112 may include one or more software modules that enable the various features and functions of the invention. Non-limiting examples of the software modules of application 112 may include one or more of a test management module 130, a respiration signal analysis module 132, an olfactory stimuli control module 134, a visual/other stimulus control module 136, a response data collection module 138, a reporting module 140, and/or other modules 142, as described herein.

Test management module 130 may include one or more sub-modules for managing the setup of tests for various test subjects, performing calibration and/or pre-testing functions, administering the tests to test subjects, and/or performing other functions. Other modules of application 112 may include sub-modules as well. Furthermore, it should be understood that, in some implementations, any items described as sub-modules may themselves me modules of application 112.

Test setup sub-module 130a may enable management of the setup of tests for various test subjects. Test setup sub-module 130a may enable selection of one or more tests (including one or more of olfactory, visual and/or other stimuli) to be administered to a test subject from test management database 190a. In some implementations, test setup sub-module 130a may also obtain one or more of stimuli presentation properties, information relating to properties/parameters associated with olfactory stimuli and/or olfactory stimuli dispenser, output presentation properties, associated with the selected tests, and/or other properties from test management database 190a. In some implementations, test setup sub-module 130a may collect various profile information regarding the test subject including, but not limited to, name, age, gender, and/or other profile information. In some implementations, test setup sub-module 130a may enable selection of one or more tests to be administered to the test subject based on the test subject's profile information. In some implementations, test setup sub-module 130a may direct storage of the collected profile information in test subject information database 190b.

It should be understood that discussion of selection or the enablement of selection as discussed herein may, in some implementations, include the receipt of a selection from among a plurality of choices from a user (e.g., a test coordinator or worker, a medical professional, an administrator, or other person). It should also be understood that discussion of selection or the enablement of selection as discussed herein may, in some implementations, include automatic or computer enabled selection from among a plurality of choices or determination of a selection.

In some implementations, calibration sub-module 130b may perform various calibration and/or pre-testing functions. Calibration sub-module 130b may adjust various sensors and/or devices to an environment (and/or context), adjust various sensors and/or devices to a test subject within the environment, and determine a baseline emotional level for the test subject within the environment.

For example, when calibrating to an environment such as a room, vehicle, simulator, kiosk, or other environment where the test is to be administered, calibration sub-module 130b may measure ambient conditions or parameters (e.g., light intensity, background noise, temperature, olfactory aspects etc.), and if necessary, may adjust the ambient conditions or parameters to ensure that meaningful data can be acquired from the test subject. In some implementations, ambient conditions or parameters may indicate environmental contamination due to olfactory residue in the olfactory stimuli dispenser 170 and/or in the air around the olfactory stimuli dispenser/subject from a prior test, and the calibration sub-module 130b may control the neutralizing air generator 175g to generate a chemical and/or pure air to neutralize/purge the olfactory residue.

In some implementations, one or more sensors or devices may be adjusted or calibrated to the test subject by calibration sub-module 130b. For the acquisition of eye data, for example, the test subject may be positioned (e.g., sitting, standing, or otherwise) so that eye tracking device 150 has an unobstructed view of either the test subject's left eye, right eye, or both eyes. Calibration sub-module 130b may generate calibration-related instructions or messages that may be presented to the test subject via one or more output devices 180 (e.g., the test subject may be instructed to move closer to or further from the eye tracking device 150). Eye tracking device 150 may also self-adjust to ensure an unobstructed view of either the subject's left eye, right eye, or both eyes. Eye tracking device 150 may be calibrated to ensure that the image of a single eye or both eyes of a test subject are clear, focused, and suitable for tracking eye properties of interest.

In some implementations, calibration sub-module 130b may also adjust a test subject's emotional level to ensure that the test subject is in an emotionally neutral state (and/or other desired emotional state) prior to presenting stimuli associated with an emotional response test to be administered. For example, a calm soothing voice may instruct the test subject to close his eyes and relax for a few moments. In some implementations, calibration sub-module 130b may present to a test subject and/or expose a test subject to one or more visual, olfactory, and/or other stimuli known to elicit neutral responses based on known emotional models. Eye tracking device 150 may measure the test subject's eye data (e.g., eye position/movement, blink data, and/or pupil dilation) corresponding to the stimuli and the eye data may be analyzed and processed to determine the subject's emotional response. In some implementations, the test subject may be presented with the emotionally neutral stimuli until the blink rate pattern, pupil response, and/or other eye properties indicate that the test subject has reached a desired emotionally neutral state.

In some implementations, calibration module 130b may also enable calibration of any number of sensors or devices (e.g., respiratory measuring device, distance detection device, emotion detection sensor, microphone, and/or other sensors/devices). As such, calibration module 130b may ensure that accurate data can be acquired when administering one or more tests. For example, one or more microphone(s) 175f for speech or other audible input may be calibrated to ensure that a subject's speech is acquired under optimal conditions, at an adequate level, or otherwise. During the calibration, distance detection device 175b may determine the distance between the nozzle of olfactory stimuli dispenser 170 and the nose of the test subject, and may further establish the determined distance as a reference distance. During the calibration, respiratory measuring device 175a may be adjusted based on physical and/or other attributes of a test subject, including but not limited to, size, weight, age, and/or other attributes.

Additional details on these and other functions performed during calibration are discussed in U.S. patent application Ser. No. 11/522,476, entitled "System and Method for Determining Human Emotion by Analyzing Eye Properties," filed Sep. 18, 2006, and in U.S. patent application Ser. No. 12/170,059, entitled "System and Method for Calibrating and Normalizing Eye Date in Emotional Testing," filed on Jul. 9, 2008, each of the disclosures of which are hereby incorporated herein by reference in their entireties. In some implementations, calibration sub-module 130b may direct the storage of the foregoing calibration data associated with the system and/or the test subjects in a calibration database 190c.

In some implementations, once the various calibration and/or pre-testing functions have been completed, the one or more selected tests may be administered to the test subject by the test setup sub-module 130a.

Figure 3:
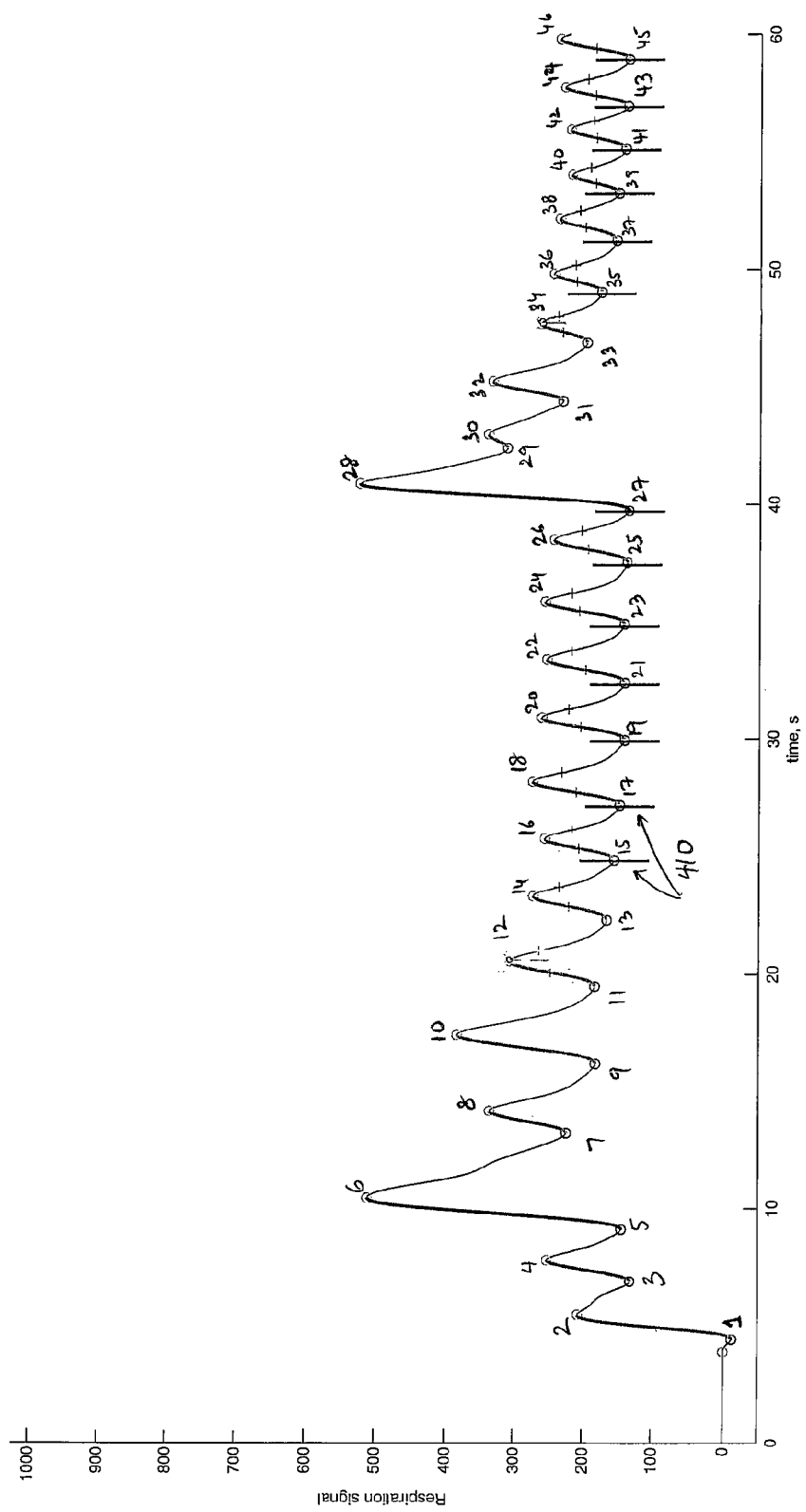
FIG. 3 depicts an exemplary respiration pattern of a test subject including inhalation and exhalation portions of the test subject's respiration cycle, according to various aspects of the invention.

In some implementations, during a test, respiration signal analysis module 132 may obtain respiratory cycle information from the respiratory measuring device 175a. From the respiratory cycle information, the respiration signal analysis module 132 may determine a respiration pattern of the test subject. The respiration pattern may include inhalation and exhalation portions of the test subject's respiration cycle. For example, in FIG. 3, portions 1-2, 3-4, 5-6, 7-8, 9-10, 11-12, 13-14, and so forth, represent inhalation portions of the test subject's respiration cycle, and portions 2-3, 4-5, 6-7, 8-9, 10-11, 12-13, 14-15, and so forth, represent the exhalation portions of the test subject's respiration cycle, wherein circles at points 3, 5, 7, 9, and so forth, indicate the beginning of an inhalation portion, circles at points 4, 6, 8, 10, and so forth, indicate the beginning of an exhalation portion. In some implementations, the respiration signal analysis module 132 may determine and/or predict a next inhalation portion of the test subject's respiration cycle such that the release of the olfactory and/or other stimulus may be timed to be in synchronization with the inhalation portion of the test subject's respiration cycle. In one implementation, the olfactory stimuli may be released at or near (e.g., slightly before to allow for travel of the olfactory stimuli to the patient) the beginning of the inhalation portion. This may ensure that different test subjects (across different tests and/or different stimuli) are exposed to the olfactory stimuli at approximately the same time during an inhalation cycle. Having substantially identical/normalized olfactory stimuli exposure conditions for different test subjects may ensure accurate emotional response determination.

Figure 4:
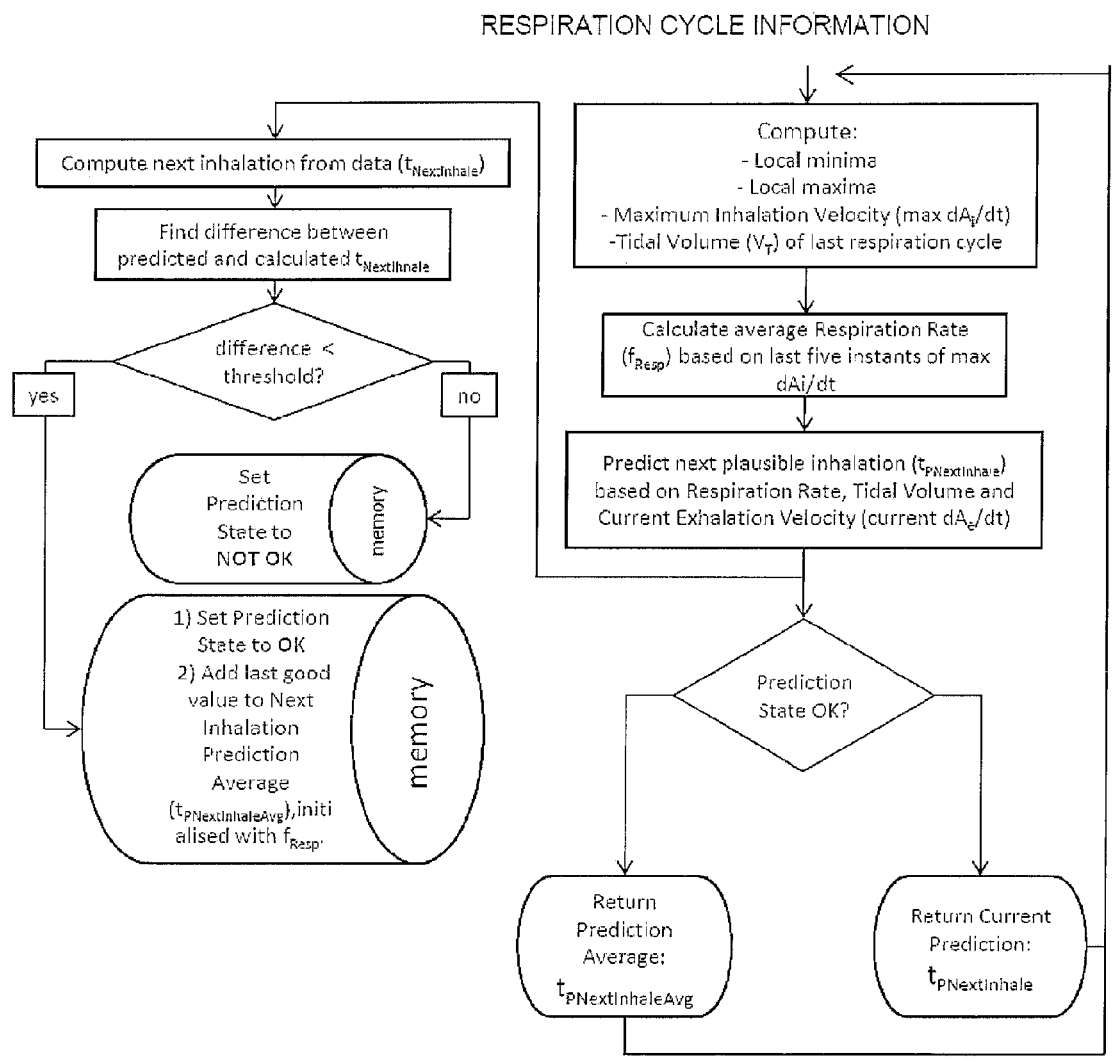
FIG. 4 depicts an exemplary breath detection algorithm, according to various aspects of the invention.

In some implementations, the respiration signal analysis module 132 may determine and/or predict a next inhalation portion of the test subject's respiration cycle based on one or more respiration parameters, for example, respiration rate, tidal volume of last respiration cycle, current exhalation velocity and/or other respiration parameters. An exemplary breath detection algorithm that may be used to determine and/or predict a next inhalation portion of the test subject's respiration cycle is depicted in FIG. 4. The algorithm utilizes various respiration parameters to determine and/or predict the next inhalation portion. Various other breath detection algorithms may be used without departing from the scope of the invention.

In some implementations, a subset of inhalation portions from the test subject's respiration cycle may be categorized as good predictions (i.e., inhalation portions which have prediction state set to OK) based on the breath detection algorithm of FIG. 4 or other algorithm. For example, in FIG. 3, vertical lines 410 at beginning of inhalation portions 15-16, 17-18, 19-20, 21-22, and so forth depict the good predictions of next inhalation portions. Accordingly, in some implementations, the release of the olfactory and/or other stimulus may be timed to be in synchronization with the good predictions of the next inhalation portions.

In some implementations, olfactory stimuli control module 134 may include one or more sub-modules for controlling the release of olfactory stimuli, analyzing the properties of the olfactory stimuli and/or olfactory stimuli dispenser, purging the olfactory stimuli residue from the environment, mixing olfactory stimuli, and/or performing other functions.

For example, an olfactory stimuli properties analysis sub-module 134a may determine aroma and/or olfactory stimuli dispenser properties prior to aroma release, such as, aroma source(s) 170a, ..., 170n, to be selected for a test, a relative volume of aroma to be dispensed from aroma source(s) 170a, ..., 170n, molecular properties of aromas in aroma source(s) 170a, ..., 170n, a desired flow rate at which aroma is to be dispensed from aroma source(s) 170a, ..., 170n, a concentration of each of the aromas that are to be mixed to generate the aroma associated with the test, the time of aroma release, and/or other properties. In some implementations, one or more of the aroma and/or olfactory stimuli dispenser properties (e.g., desired flow rate at which aroma is to be dispensed from aroma source(s)) may be fixed for each test and obtained from test management database 190a. In some implementations, one or more of the aroma and/or olfactory stimuli dispenser properties (e.g., relative volume of aroma to be dispensed from aroma source(s), desired flow rate at which aroma is to be dispensed from aroma source(s), etc.) may be modified based on the distance measured from the olfactory stimuli dispenser to the test subject by the distance detection device 175b. For instance, if a test subject is seated relatively far away from the nozzle, the flow rate at which aroma is dispensed from aroma source(s) may be higher than that for a test subject who is seated relatively closer to the nozzle. This may ensure that the intensity at which the test subjects are impacted with the olfactory stimuli remains substantially identical across different tests and/or different test subjects, and/or different stimuli.

In some implementations, the olfactory stimuli properties analysis sub-module 134a may determine aroma and/or olfactory stimuli dispenser properties at and/or after aroma release. In some implementations, olfactory stimuli properties analysis sub-module 134a may receive aroma flow rate information detected by the olfactory stimuli flow detector 172 when the aroma is released by the olfactory stimuli dispenser 170. By analyzing the flow rate information, the olfactory stimuli properties analysis sub-module 134a may determine whether the aroma was actually released by the olfactory stimuli dispenser 170, whether the aroma was released at the desired flow rate, and/or may determine other aroma and/or olfactory stimuli dispenser properties. For instance, if a determination was made that aroma was not released and/or released at a lower than desired flow rate by the olfactory stimuli dispenser 170, this may indicate that the olfactory stimuli dispenser and/or aroma source(s) may be contaminated and/or that any results recorded in relation to this non-release/altered-release may be discarded and/or discounted.

In some implementations, an olfactory stimuli release control sub-module 134b may determine a time at which the olfactory stimuli should be triggered for release to reach the subject's nose at a predetermined time, and may generate a control signal (for the controllable olfactory stimuli dispenser 170) to release the olfactory stimuli at the determined time. In some implementations, the time for release may be determined based on respiratory cycle information of a test subject. For example, olfactory stimuli release control sub-module 134b receives respiratory cycle information from the respiration signal analysis module 132, and generates a control signal to release the olfactory stimuli in relative synchronization with the test subject's respiration pattern.

In some implementations, the predetermined time may correspond to an inhalation portion of the test subject's respiration cycle (or to a projected time at which the test subject will be in an inhalation portion of the respiration cycle). For example, in FIG. 3, the predetermined time may correspond to an inhalation portion 15-16, or 17-18, or 19-20, and so forth (or a projected time at which the test subject will be in an inhalation portion 15-16, or 17-18, or 19-20, and so forth). In some implementations, the predetermined time may be a time that corresponds to the determined and/or predicted next inhalation portion of the test subject's respiration cycle, as determined by the respiration signal analysis module 132. Based, at least in part, on the respiration cycle/pattern information received from the respiration signal analysis module 132, the olfactory stimuli release control sub-module 134b may generate a control signal to release the olfactory stimuli at the determined time, such that the olfactory stimuli reaches the subjects nose at a time and/or time period when the subject is in the inhalation portion of the respiration cycle. In some implementations, the olfactory stimuli release control sub-module 134b may generate the control signal to release the olfactory stimuli at or near the beginning of the inhalation portion.

In some implementations the timing of the olfactory stimulus release may be based on various timing parameters including for example, the distance from the nozzle of the olfactory stimuli dispenser 170 to the subject's nose, the desired flow rate of the olfactory stimulus to be released from the olfactory stimuli dispenser, and/or other timing parameters. For example, based on the distance measurement from the distance detection device 175b and the desired flow rate information from the olfactory stimuli properties analysis module 134a, the olfactory stimuli release control sub-module 134b may determine the time at which the olfactory stimulus should be triggered for release to reach the subject's nose at a predetermined time. In some implementations, the predetermined time may correspond to an inhalation portion of the test subject's respiration cycle (or to a projected time at which the test subject will be in an inhalation portion of the respiration cycle). Based, at least in part, on the respiration cycle/pattern information, the distance measurement and the desired flow rate information, the olfactory stimuli release control sub-module 134b may generate a control signal to release the olfactory stimuli at the determined time, such that the olfactory stimuli reaches the subject's nose at a time and/or time period when the subject is in the inhalation portion of the respiration cycle. As discussed herein, these features enable specific control of (and thus, modulation of) delivery of olfactory stimuli to test subjects as well as synchronized/normalized delivery of olfactory stimuli across multiple test subjects, which may render test results more meaningful/useful.

In some implementations, the control signal generated by the olfactory stimuli release control sub-module 134b may identify one or more aroma sources 170a, . . . 170n, from which olfactory stimuli is to be dispensed, the desired flow rate at which the olfactory stimuli is to be dispensed, and/or other information.

In some implementations, an olfactory stimuli purging sub-module 134c may receive environmental parameters measured by environment sensor 175c. In some implementations, the olfactory stimuli purging sub-module 134c may detect, in between stimuli and/or in between tests, environmental contamination due to olfactory residue in the olfactory stimuli dispenser and/or in the air around the olfactory stimuli dispenser/subject. In some implementations, the olfactory stimuli purging sub-module may detect, prior to, during, and/or after the emotional response test, environmental contamination due to the olfactory residue. In some implementations, in response to such determination, the olfactory stimuli purging sub-module 134c may control a neutralizing air generator that generates a chemical and/or pure air to neutralize/purge the olfactory residue.

In some implementations, the olfactory stimuli release control sub-module 134b may receive a signal from the olfactory stimuli purging sub-module 134c indicating environmental contamination, and in response thereto, the olfactory stimuli release control sub-module 134b may not generate a control signal to release the olfactory stimuli because the release of olfactory stimuli may generate flawed results.

In some implementations, olfactory stimuli mixing module 134d may generate a signal (for olfactory stimuli dispenser 170) to mix olfactory stimuli, for example, aromas. In some implementations, the olfactory stimuli mixing module may generate a signal to mix aromas from two or more aroma sources 170a, . . . 170n, such that a desired aroma is generated. Aromas may be mixed in desired and/or pre-determined concentrations. In some implementations, olfactory stimuli mixing module 134d may obtain aroma and/or olfactory stimuli dispenser properties from test management database 190a and/or olfactory stimuli properties analysis module 134a. In some implementations, based on one or more aroma and/or olfactory stimuli dispenser properties (e.g., aroma source(s) to be selected to generate the aroma associated with a test, the concentration of each of the aromas that are to be mixed to generate the aroma associated with the test, etc.), olfactory stimuli mixing module 134d may generate a signal to mix the aromas at the respective concentrations. In some implementations, the mixed aroma is maintained in a receptacle (not shown) in the olfactory stimuli dispenser 170 and the control signal generated by the olfactory stimuli release control sub-module 134b may identify the receptacle from which mixed aroma is to be dispensed, the desired flow rate at which the aroma is to be dispensed, and/or other information.

In some implementations, visual/other stimuli control module 136 may facilitate the presentation of visual and/or other stimuli associated with the test to be administered to the test subject. In some implementations, the exposure of the test subject to visual and/or other stimuli may be timed to be in synchronization with the release of the olfactory stimuli. For example, based on the respiration cycle/pattern information (and/or distance or flow rate information), a time for release for each of olfactory, visual, and/or other stimuli may be determined, such that each of these stimuli impact the test subject at approximately the same time (for example, at a time and/or time period when the test subject is in the inhalation portion of the respiration cycle). If both an olfactory and a visual stimulus are to be presented to the test subject at the same time, the exposure of the visual stimulus may be delayed to account for the time the olfactory stimulus may take to reach the test subject's nose.

In some implementations, response data collection module 138 may collect eye data tracked/measured by eye tracking device 150 in response to the presentation of one or more visual, olfactory, and/or other stimuli to test subjects. Response data collection module 138 may also collect other physiological data regarding the subject's response to stimuli from one or more emotion detection sensors 175d. Response data collection module 138 may direct storage of the collected data in collected response data database 190d.

Figure 5A:
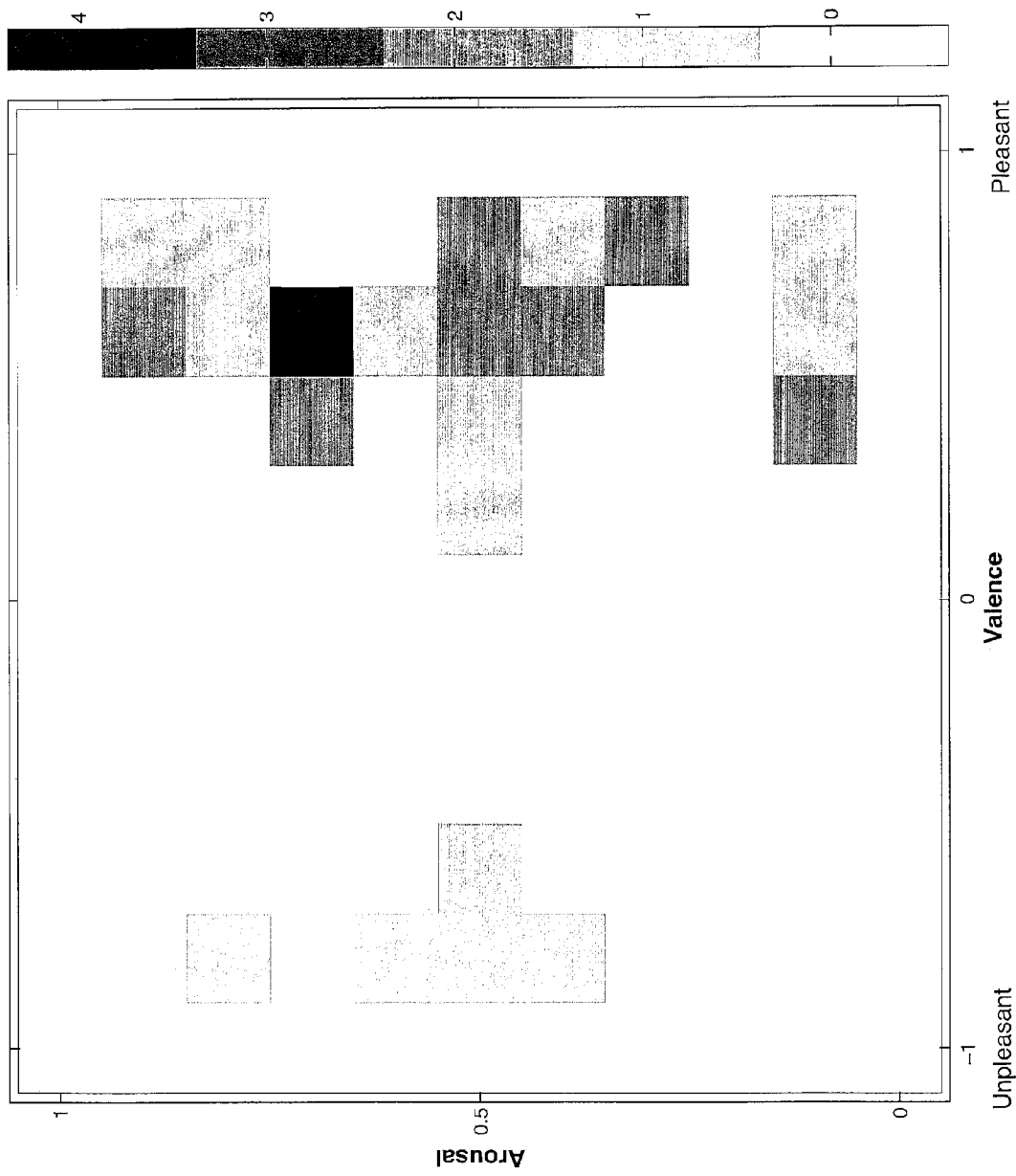
FIGS. 5a and 5b depict maps regarding the test subjects' emotional response to the olfactory stimuli, according to various aspects of the invention.
Figure 5B:
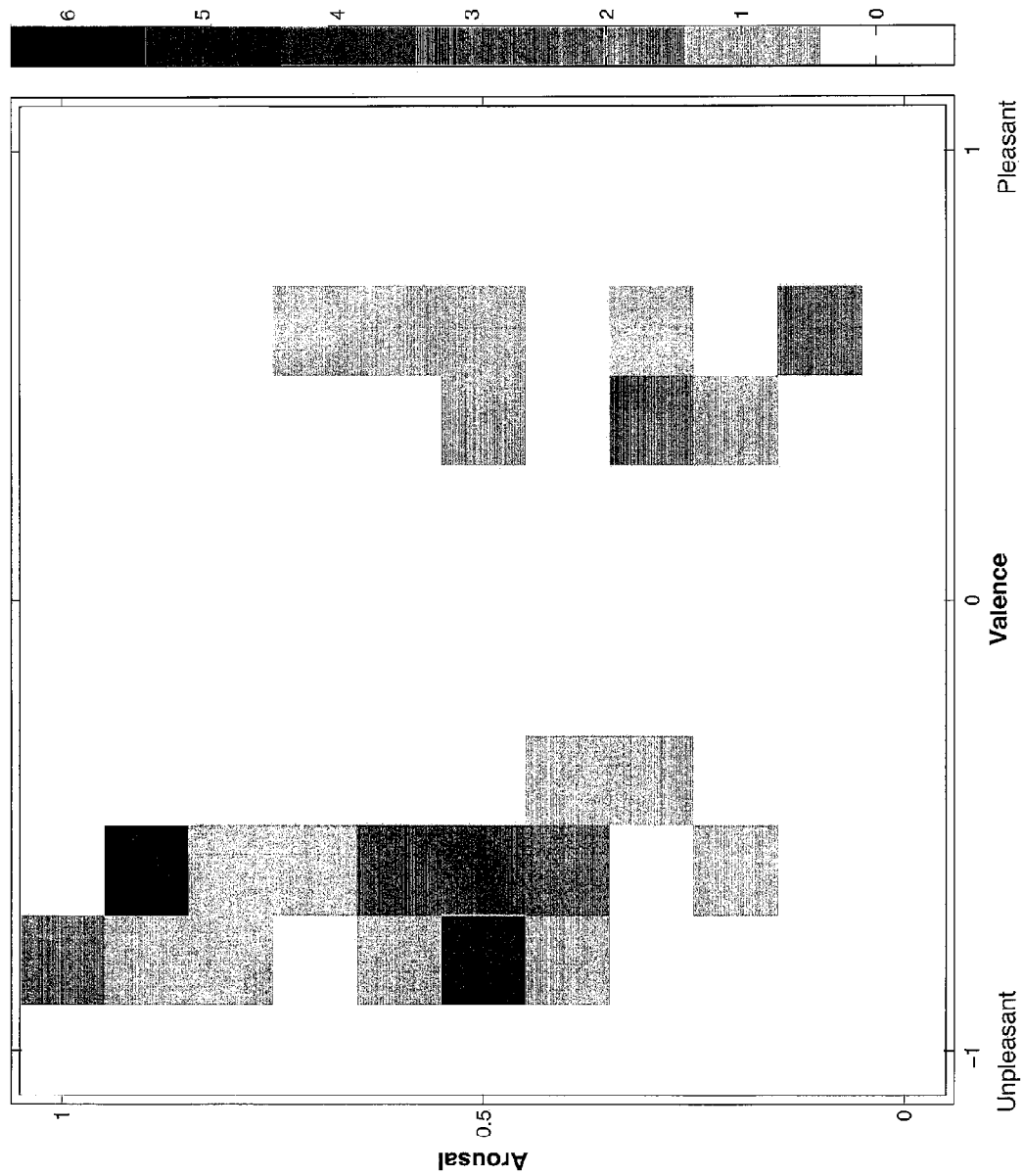

In some implementations, reporting module 140 may generate reports and/or maps regarding the test subject's emotional response to the presented stimuli. Exemplary maps are depicted in FIGS. 5a and 5b. Maps in FIGS. 5a and 5b, for example, plot the emotional valence and emotional arousal components of the test subject's emotional response to the olfactory stimuli. FIG. 5a plots the emotional valence on a scale of −1 to 1, and emotional arousal on a scale of 0-4, where 0 represents minimum intensity and 4 represents maximum intensity. FIG. 5b plots the emotional valence on a scale of −1 to 1, and emotional arousal on a scale of 0-6, where 0 represents minimum intensity and 6 represents maximum intensity. Other scales and/or ranges may be used. Various techniques may be used for depicting the valence and arousal, for example, shades of gray, color, indicia, and/or other techniques representing various intensities. Other mapping/plotting techniques may be used, for example, pie charts, bar graphs, and/or other techniques.

In some implementations, an emotional response/emotion tool measuring system 120 may also execute on computer 110 or another computer. The emotional response measuring system 120 may determine a subject's emotional response to olfactory, visual, and/or other stimuli. Emotional response measuring system 120 may include an emotional response determination module 120a, and/or other modules 120b.

In some implementations, emotional response determination module 120a may determine information regarding the test subject's emotional response to the stimuli presented during the tests, from the eye data measured by the eye tracking device 150.

In some implementations, distance detection device 175b and respiratory measuring device 175a may continue to measure the distance between the nozzle of the olfactory stimuli dispenser and the subject's nose and the respiratory cycle information of the test subject after the release of the olfactory stimulus. Based on the distance data and the aroma flow information measured by the olfactory stimuli flow detector 172 at the time of aroma release, the time at which the aroma actually reached the subject's nose (i.e., actually impacted the subject) can be determined. This data may be used to assess whether the distance varied from the time the olfactory stimuli was released to the time the olfactory stimulus actually impacted the subject, whether the respiration varied from the time the olfactory stimuli was released to the time the olfactory stimulus actually impacted the subject, and/or whether the flow rate at which the olfactory stimuli was released from the olfactory stimuli dispenser varied from the desired flow rate and/or other variations. In some implementations, the various variations may be compensated for when determining an emotional response.

In some implementations, because the time at which olfactory stimuli actually impacted the test subject may be determined as described above, the corresponding measured eye data may be analyzed by the emotional response determination module 120a to determine the test subject's emotional response to the olfactory stimuli. Because the test subject may be presented with visual stimuli and olfactory stimuli during a given test, the subject's emotional response to the olfactory stimuli and the subject's emotional response to the visual and/or other stimuli may be differentiated from one another.

In some implementations, distance detection device 175b may continue to measure the distance between the nozzle of olfactory stimuli dispenser 170 and the subject's nose at and/or after it has been determined that the olfactory stimuli has reached the subjects nose and/or that the subject has detected the aroma. In some instances, this data may be utilized, at least in part, to determine/measure an emotional response to the olfactory stimuli. For example, any variance in the distance between the nozzle of olfactory stimuli dispenser 170 and the subject's nose may be an indicator of an emotional response (e.g., the subject has either instinctually or rationally recoiled from or moved towards the olfactory stimuli). In some implementations, other parameters/measurements may be made at and/or after it has been determined that the olfactory stimuli has reached the subjects nose and/or that the subject has detected the aroma.

Those of ordinary skill in the art will appreciate that the systems described herein are examples and that the system of the invention may include more or less of the described components/elements and that the features and functions described herein may be performed by components different from those described herein. In some implementations the functions of certain components and/or may be combined.

Figure 2:
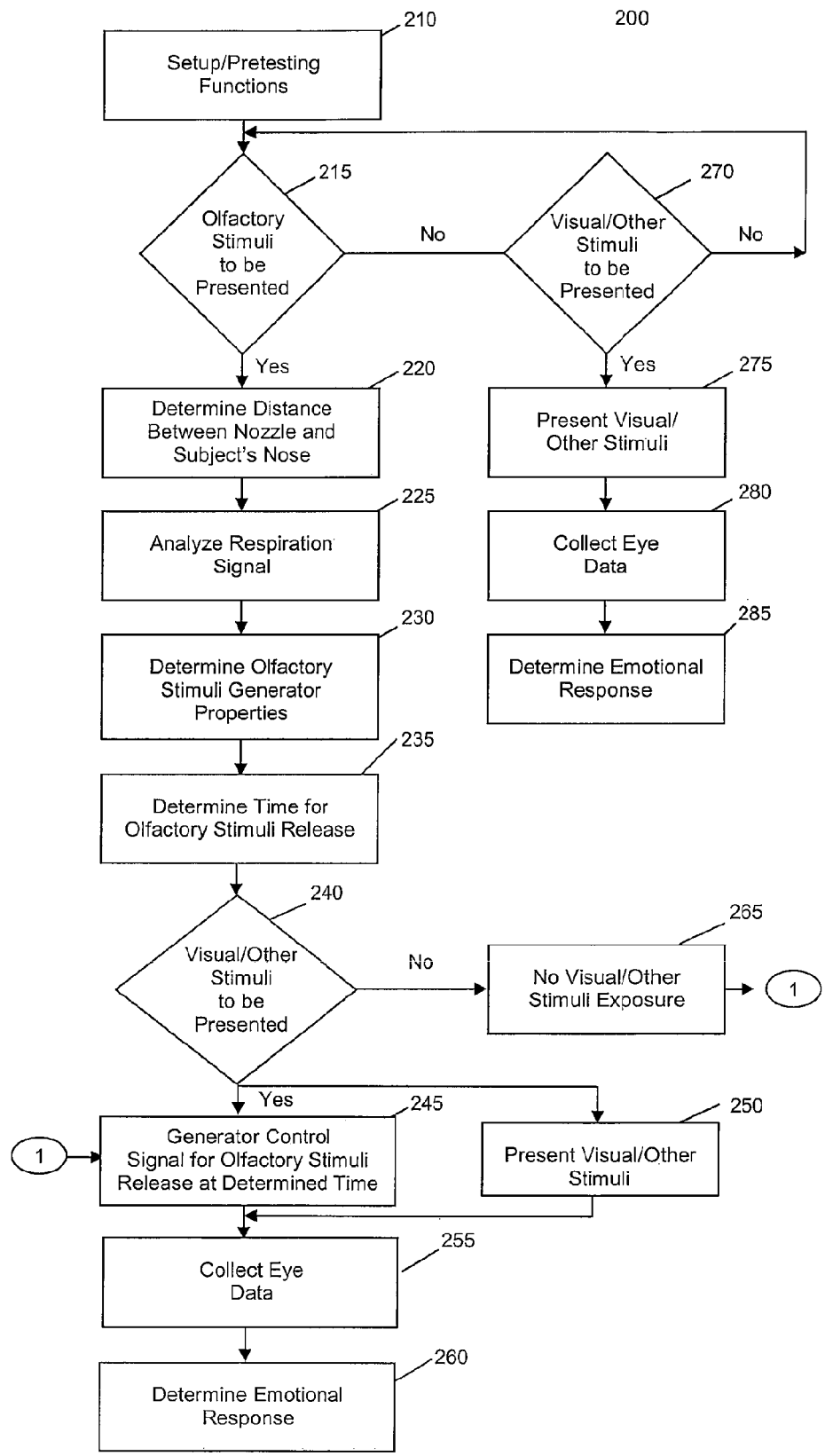
FIG. 2 illustrates an exemplary method for determining emotional response to olfactory stimuli, according to various aspects of the invention.

FIG. 2 illustrates an exemplary flowchart of processing operations, according to various aspects of the invention. The described operations may be accomplished using some of all of the system components described in detail above and, in some implementations, various operations may be performed in different sequences. In other implementations, additional operations may be performed along with some or all of the operations shown in FIG. 2. In yet other implementations, one or more operations may be performed simultaneously. Accordingly, the operations described are exemplary in nature and, as such, should not be viewed as limiting.

In an operation 210, various setup and/or pre-testing operations may be performed (e.g., performed by the test management module 130).

In an operation 215, a determination may be made as to whether the test subject is to be presented with olfactory stimuli (e.g., by test management module 130). If one or more olfactory stimuli are associated with a particular test selected for a test subject, it may be determined that the test subject is to be presented with olfactory stimuli.

If a determination is made that the test subject is to be presented with olfactory stimuli in operation 215, then processing may continue to an operation 220, where a distance between the nozzle of olfactory stimuli dispenser 170 and the test subject's nose may be measured (e.g., by the distance detection device 175b).

In an operation 225, the test subject's respiratory cycle information may be analyzed (e.g., by the respiration signal analysis module 132) to determine the test subject's respiration pattern (including inhalation and exhalation portions of the test subject's respiration cycle).

In an operation 230, aroma and/or olfactory stimuli dispenser properties, for example, a desired flow rate of the olfactory stimulus to be released from the olfactory stimuli dispenser 170 may be determined (e.g., by the olfactory stimuli properties analysis sub-module 134a).

In an operation 235, a time ($T_R$) at which the olfactory stimulus is to be triggered for release to reach the subject's nose at a predetermined time ($T_{PD}$) may be determined (e.g., by olfactory stimuli release control sub-module 134b). In some implementations, this determination may be based at least in part on the respiration cycle information of a test subject. In some instances, the predetermined time ($T_{PD}$) may correspond to an inhalation portion of the test subject's respiration cycle or to a projected time at which the subject will be in an inhalation portion of the respiration cycle. In some implementations, the timing of the stimulus release may be based on various timing parameters including for example, the distance from the nozzle of the olfactory stimulus dispenser to the nose of the test subject, a desired flow rate of the olfactory stimulus to be released from the olfactory stimulus dispenser, and/or other timing parameters.

In one example, based at least in part on respiratory cycle information, a desired flow rate of the olfactory stimuli, and the distance from the nozzle of the olfactory stimulus dispenser to the subject's nose, a time ($T_R$) at which the olfactory stimulus should be triggered for release to reach the subject's nose at a predetermined time ($T_{PD}$) may be determined.

In an operation 240, a determination may be made as to whether the test subject is to be presented with one or more visual and/or other stimuli along with the olfactory stimuli. If a determination is made that one or more visual and/or other stimuli is to be presented in operation 240, such stimuli may be presented to the test subject in an operation 250, and a control signal may be generated for an olfactory stimulus dispenser (e.g., olfactory stimulus dispenser) 170 to release the olfactory stimulus at the determined time ($T_R$), in an operation 245. In some implementations, the control signal may be generated to release the olfactory stimulus at the determined time, such that the olfactory stimuli reaches the subject's nose at a time and/or time period when the subject is in the inhalation portion of the respiration cycle.

If a determination is made in operation 240 that visual and/or other stimuli is not be presented, then processing may continue to an operation 265, where no visual and/or other stimuli is presented. Processing may then continue to operation 245 where a control signal may be generated for olfactory stimulus dispenser 170 to release the olfactory stimulus at the determined time ($T_R$).

In an operation 255, subject's eye data in response to the olfactory, visual, and/or other stimulus may be measured (e.g., by eye tracking device 150). Other physiological data regarding the subjects response may also be collected (e.g., by one or more emotion detection sensors 175d). The measured eye data and/or other physiological data regarding the test subject's response to the olfactory, visual and/or other stimulus may be collected (e.g., by response data collection module 138). As discussed herein, in some instances the distance between the subject's nose (or other body part) and the olfactory stimuli dispenser may be measured (e.g., by distance detection device 175*b*) after the olfactory stimuli has impacted the subject and may be used to determine an emotional response.

Also as noted herein, in some implementations, the measurement of data in response to various stimuli may be timed to correspond to the determined time that certain stimuli (e.g., olfactory stimuli) reach the nose/respiratory system of, or are otherwise detected by, the subject. The time that certain stimuli (e.g., olfactory stimuli) reach the nose/respiratory system of, or are otherwise detected by, the subject may be determined using various parameters such as, for example, distance between a nozzle of an olfactory stimuli generator (e.g., olfactory stimuli generator 170) and the nose of the subject, the flow rate at which the olfactory stimuli are released from olfactory stimuli generator 170, environmental parameters, and/or other parameters.

In an operation 260, the subject's emotional response to the olfactory, visual, and/or other stimulus may be determined (e.g., by the emotional response determination module 120*a*).

If a determination is made that the test subject is not to be presented with olfactory stimuli in operation 215, the processing may continue to an operation 270, where a determination is made whether the test subject is to be presented with one or more visual and/or other stimuli. If a determination is made that one or more visual and/or other stimuli is to be presented in operation 270, such stimuli are presented to the test subject in operation 275, eye data corresponding to the subject's response to the visual and/or other stimuli is collected in operation 280 and the subject's emotional response to the visual and/or other stimuli is determined in operation 285.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A method of determining an emotional response to olfactory stimuli presented to a test subject during an emotional response test, the method comprising:
    analyzing respiration cycle information associated with the test subject to determine a respiration pattern that includes inhalation and exhalation portions of the test subject's respiration cycle;
    measuring a distance between a nozzle of an olfactory stimuli dispenser configured to controllably release an olfactory stimulus and the test subject's nose;
    determining a desired flow rate at which the olfactory stimulus is to be released;
    determining, based at least in part on the respiration cycle information, the measured distance, and the desired flow rate, a time at which the olfactory stimulus should be triggered for release to reach the test subject's nose at a predetermined time, the predetermined time corresponding to an inhalation portion of the test subject's respiration cycle or to a projected time at which the test subject will be in an inhalation portion of the respiration cycle;
    controllably releasing the olfactory stimulus at the determined time;
    receiving, at a computer, from an eye-tracking device operatively coupled to the computer, eye data collected from the test subject by the eye-tracking device while the test subject is presented with the released olfactory stimulus, the eye data including pupil data, blink data, and gaze data; and
    processing, by the computer, the collected eye data to determine the test subject's emotional response to the olfactory stimulus.

2. A method of determining an emotional response to olfactory stimuli presented to a test subject during an emotional response test, the method comprising:
    analyzing respiration cycle information associated with the test subject to determine a respiration pattern that includes inhalation and exhalation portions of the test subject's respiration cycle;
    determining, based at least in part on the respiration cycle information, a time at which an olfactory stimulus should be triggered for release to reach the test subject's nose at a predetermined time, the predetermined time corresponding to an inhalation portion of the test subject's respiration cycle or to a projected time at which the test subject will be in an inhalation portion of the respiration cycle;
    controllably releasing the olfactory stimulus at the determined time;
    receiving, at a computer, from an eye-tracking device operatively coupled to the computer, eye data collected from the test subject by the eye-tracking device while the test subject is presented with the released olfactory stimulus, the eye data including pupil data, blink data, and gaze data;
    processing, by the computer, the collected eye data to determine the test subject's emotional response to the olfactory stimulus;
    measuring, after the release of the olfactory stimulus, a distance between a nozzle of an olfactory stimuli dispenser configured to controllably release the olfactory stimulus and the test subject's nose;
    detecting flow rate information associated with the released olfactory stimulus; and
    determining, based at least in part on the measured distance and the detected flow rate information, a time at which the olfactory stimulus actually reached the subject's nose; and
    wherein processing the collected eye data to determine the test subject's emotional response to the olfactory stimulus is based at least in part on the determined time at which the olfactory stimulus actually reached the test subject's nose.

3. A method of determining an emotional response to olfactory stimuli presented to a test subject during an emotional response test, the method comprising:
    analyzing respiration cycle information associated with the test subject to determine a respiration pattern that includes inhalation and exhalation portions of the test subject's respiration cycle;
    determining, based at least in part on the respiration cycle information, a time at which an olfactory stimulus should be triggered for release to reach the test subject's nose at a predetermined time, the predetermined time corresponding to an inhalation portion of the test subject's respiration cycle or to a projected time at which the test subject will be in an inhalation portion of the respiration cycle;
    controllably releasing the olfactory stimulus at the determined time;

receiving, at a computer, from an eye-tracking device operatively coupled to the computer, eye data collected from the test subject by the eye-tracking device while the test subject is presented with the released olfactory stimulus, the eye data including pupil data, blink data, and gaze data;

processing, by the computer, the collected eye data to determine the test subject's emotional response to the olfactory stimulus;

detecting, prior to, during, and/or after the emotional response test, environmental contamination due to olfactory residue in an olfactory stimuli dispenser and/or in air around the olfactory stimuli dispenser or subject; and neutralizing and/or purging the olfactory residue.

4. The method of claim 3, further comprising:

measuring the test subject's physiological responses to the released olfactory stimulus; and wherein determining the test subject's emotional response to the olfactory stimulus is based at least in part on the test subject's measured physiological responses to the released olfactory stimulus.

5. A system for determining an emotional response to olfactory stimuli presented to a test subject during an emotional response test, the system comprising:

a distance detection device configured to measure a distance between a nozzle of an olfactory stimuli dispenser configured to controllably release an olfactory stimulus and the test subject's nose; and a non-transitory computer-readable storage medium, the computer-readable storage medium storing one or more software modules comprising computer-readable instructions executable by a processor, the one or more software modules comprising:

a respiration signal analysis module comprising computer-readable instructions configured to analyze respiration cycle information associated with the test subject to determine a respiration pattern that includes inhalation and exhalation portions of the test subject's respiration cycle;

an olfactory stimuli properties analysis module comprising computer-readable instructions configured to determine a desired flow rate at which the olfactory stimulus is to be released;

an olfactory stimuli control module comprising computer-readable instructions configured to:

(i) determine, based at least in part on the respiration cycle information, the measured distance, and the desired flow rate, a time at which the olfactory stimulus should be triggered for release to reach the test subject's nose at a predetermined time, the predetermined time corresponding to an inhalation portion of the test subject's respiration cycle or to a projected time at which the test subject will be in an inhalation portion of the respiration cycle; and (ii) controllably release the olfactory stimulus at the determined time;

a response data collection module comprising computer-readable instructions configured to obtain eye data collected from the test subject while the test subject is presented with the released olfactory stimulus, the eye data including pupil data, blink data, and gaze data; and an emotional response determination module comprising computer-readable instructions configured to process the collected eye data to determine the test subject's emotional response to the olfactory stimulus.

6. A system for determining an emotional response to olfactory stimuli presented to a test subject during an emotional response test, the system comprising:

a distance detection device configured to measure, after release of an olfactory stimulus, a distance between a nozzle of an olfactory stimuli dispenser configured to controllably release the olfactory stimulus and the test subject's nose;

an olfactory stimuli flow detector configured to detect flow rate information associated with the released olfactory stimulus; and a non-transitory computer-readable storage medium, the computer-readable storage medium storing one or more software modules comprising computer-readable instructions executable by a processor, the one or more software modules comprising:

a respiration signal analysis module comprising computer-readable instructions configured to analyze respiration cycle information associated with the test subject to determine a respiration pattern that includes inhalation and exhalation portions of the test subject's respiration cycle;

an olfactory stimuli control module comprising computer-readable instructions configured to:

(i) determine, based at least in part on the respiration cycle information, a time at which the olfactory stimulus should be triggered for release to reach the test subject's nose at a predetermined time, the predetermined time corresponding to an inhalation portion of the test subject's respiration cycle or to a projected time at which the test subject will be in an inhalation portion of the respiration cycle; and (ii) controllably release the olfactory stimulus at the determined time;

a response data collection module comprising computer-readable instructions configured to obtain eye data collected from the test subject while the test subject is presented with the released olfactory stimulus, the eye data including pupil data, blink data, and gaze data;

an emotional response determination module comprising computer-readable instructions configured to process the collected eye data to determine the test subject's emotional response to the olfactory stimulus;

an olfactory stimuli properties analysis module comprising computer-readable instructions configured to determine, based at least in part on the measured distance and the detected flow rate information, a time at which the olfactory stimulus actually reached the subject's nose; and wherein the emotional response determination module comprises computer-readable instructions configured to process the collected eye data to further determine the test subject's emotional response to the olfactory stimulus based at least in part on the determined time at which the olfactory stimulus actually reached the test subject's nose.

7. A system for determining an emotional response to olfactory stimuli presented to a test subject during an emotional response test, the system comprising:

a non-transitory computer-readable storage medium, the computer-readable storage medium storing one or more software modules comprising computer-readable instructions executable by a processor, the one or more software modules comprising:

a respiration signal analysis module comprising computer-readable instructions configured to analyze respiration cycle information associated with the test subject to determine a respiration pattern that includes inhalation and exhalation portions of the test subject's respiration cycle;

an olfactory stimuli control module comprising computer-readable instructions configured to:
(i) determine, based at least in part on the respiration cycle information, a time at which an olfactory stimulus should be triggered for release to reach the test subject's nose at a predetermined time, the predetermined time corresponding to an inhalation portion of the test subject's respiration cycle or to a projected time at which the test subject will be in an inhalation portion of the respiration cycle; and
(ii) controllably release the olfactory stimulus at the determined time;

a response data collection module comprising computer-readable instructions configured to obtain eye data collected from the test subject while the test subject is presented with the released olfactory stimulus, the eye data including pupil data, blink data, and gaze data;

an emotional response determination module comprising computer-readable instructions configured to process the collected eye data to determine the test subject's emotional response to the olfactory stimulus; and an olfactory stimuli purging module comprising computer-readable instructions configured to:
(i) detect, prior to, during, and/or after the emotional response test, environmental contamination due to olfactory residue in an aroma dispenser and/or in air around the olfactory stimuli dispenser or subject; and
(ii) neutralize and/or purge the olfactory residue.

8. The system of claim 7, further comprising:
one or more emotion detection sensors configured to measure the test subject's physiological responses to the released olfactory stimulus, and
wherein the emotional response determination module comprises computer-readable instructions configured to further determine the test subject's emotional response to the olfactory stimulus based at least in part on the test subject's measured physiological responses to the released olfactory stimulus.

* * * * *